US010309957B2

(12) United States Patent
Tanigawara et al.

(10) Patent No.: US 10,309,957 B2
(45) Date of Patent: Jun. 4, 2019

(54) METHOD FOR DETERMINING SENSITIVITY TO FLUOROURACIL IN A SUBJECT HAVING COLORECTAL CANCER

(71) Applicants: KEIO UNIVERSITY, Tokyo (JP); KABUSHIKI KAISHA YAKULT HONSHA, Tokyo (JP)

(72) Inventors: Yusuke Tanigawara, Kawasaki (JP); Akito Nishimuta, Bunkyo-ku (JP); Yuki Otani, Sapporo (JP); Mitsuhisa Matsuo, Chiba (JP)

(73) Assignees: KEIO UNIVERSITY, Tokyo (JP); KABUSHIKI KAISHA YAKULT HONSHA, Tokyo (JP)

( * ) Notice: Subject to any disclaimer, the term of this patent is extended or adjusted under 35 U.S.C. 154(b) by 0 days.

(21) Appl. No.: 15/708,178

(22) Filed: Sep. 19, 2017

(65) Prior Publication Data

US 2018/0038848 A1     Feb. 8, 2018

Related U.S. Application Data

(62) Division of application No. 14/007,145, filed as application No. PCT/JP2012/054633 on Feb. 24, 2012, now Pat. No. 9,797,884.

(30) Foreign Application Priority Data

Mar. 24, 2011    (JP) ................... 2011-065993

(51) Int. Cl.
| | |
|---|---|
| *A61K 31/132* | (2006.01) |
| *G01N 33/50* | (2006.01) |
| *G01N 33/574* | (2006.01) |
| *A61K 45/06* | (2006.01) |
| *A61K 31/282* | (2006.01) |
| *A61K 31/515* | (2006.01) |
| *A61K 31/198* | (2006.01) |
| *A61K 31/513* | (2006.01) |
| *A61K 31/555* | (2006.01) |
| *A61K 31/7008* | (2006.01) |

(52) U.S. Cl.
CPC ....... *G01N 33/5091* (2013.01); *A61K 31/132* (2013.01); *A61K 31/198* (2013.01); *A61K 31/282* (2013.01); *A61K 31/513* (2013.01); *A61K 31/515* (2013.01); *A61K 31/555* (2013.01); *A61K 31/7008* (2013.01); *A61K 45/06* (2013.01); *G01N 33/5011* (2013.01); *G01N 33/574* (2013.01); *G01N 2500/00* (2013.01); *G01N 2800/52* (2013.01); *G01N 2800/60* (2013.01); *G01N 2800/7066* (2013.01)

(58) Field of Classification Search
None
See application file for complete search history.

(56) References Cited

U.S. PATENT DOCUMENTS

| | | | |
|---|---|---|---|
| 2005/0214878 A1 | 9/2005 | Ko et al. | |
| 2009/0075284 A1 | 3/2009 | Chinnaiyan et al. | |
| 2010/0099121 A1 | 4/2010 | Ko et al. | |
| 2010/0273732 A1* | 10/2010 | Bacopoulos | ......... A61K 9/0019 514/49 |
| 2010/0292331 A1 | 11/2010 | Mitchell et al. | |
| 2010/0323034 A1 | 12/2010 | Tanigawara et al. | |
| 2011/0003842 A1 | 1/2011 | Tanigawara et al. | |
| 2011/0085981 A1 | 4/2011 | Wang | |
| 2012/0214831 A1 | 8/2012 | Tanigawara et al. | |
| 2012/0220613 A1 | 8/2012 | Tanigawara et al. | |
| 2012/0220618 A1 | 8/2012 | Tanigawara et al. | |
| 2013/0115649 A1* | 5/2013 | Shuster | .............. G01N 33/5091 435/29 |

FOREIGN PATENT DOCUMENTS

| | | | | |
|---|---|---|---|---|
| CN | 101363837 | A | 2/2009 | |
| CN | 101639445 | A | 2/2010 | |
| CN | 101932338 | A | 12/2010 | |
| CN | 101932939 | A | 12/2010 | |
| CN | 102597762 | A | 7/2012 | |
| EP | 2 233 589 | A1 | 9/2010 | |
| EP | 2 241 334 | A1 | 10/2010 | |
| JP | 2004-257783 | A | 9/2004 | |
| JP | 2008-249716 | A | 10/2008 | |
| JP | 2008-309501 | A | 12/2008 | |
| JP | 2009-018999 | A | 1/2009 | |
| JP | 2010-504527 | A | 2/2010 | |
| JP | 4621592 | B2 | 11/2010 | |
| WO | WO 2005/024419 | A1 | 3/2005 | |
| WO | WO 2007/124314 | A2 | 11/2007 | |
| WO | WO-2008036691 | A2 * | 3/2008 | ....... G01N 33/57434 |
| WO | WO 2009/015491 | A1 | 2/2009 | |
| WO | WO 2009/096196 | A1 | 8/2009 | |
| WO | WO-2011052750 | A1 * | 5/2011 | ......... A61K 31/4745 |

OTHER PUBLICATIONS

Translation of WO-2011052750-A1 published May 2011, provided by the JPO (Year: 2011).*
International Search Report and Written Opinion dated May 22, 2012 in PCT/JP2012/054633.
E. Michael August, et al., "Inhibition of Fibroblast Hyaluronic Acid Production by Suramin" Oncology Research, vol. 5, No. 10-11, 1993 pp. 415-422.
Shin Yazawa, et al., "Tumor-related expression of α1,2fucosylated antigens on colorectal carcinoma cells and its suppression by cell-mediated priming using sugar acceptors for α1,2fucosyltransferase" Glycobiology, vol. 12, No. 9, 2002, pp. 545-553.
Mutsuhiro Takekawa, "Formation of stress granules regulates stress-responsive signaling and resistance of cancer cells to chemotherapy" Experimental Medicine, vol. 29, No. 2, Feb. 1, 2011, pp. 269-275 (with English Abstract).

(Continued)

*Primary Examiner* — Susan M Hanley
(74) *Attorney, Agent, or Firm* — Oblon, McClelland, Maier & Neustadt, L.L.P.

(57) ABSTRACT

To provide a marker for determining sensitivity to an anti-cancer agent, which can determine whether or not a patient has a therapeutic response to the anti-cancer agent, and cancer therapeutic means employing the marker.

2 Claims, 10 Drawing Sheets

(56) References Cited

OTHER PUBLICATIONS

Yoshinori Shirota, et al., "ERCC1 and Thymidylate Synthase mRNA Levels Predict Survival for Colorectal Cancer Patients Receiving Combination Oxaliplatin and Fluorouracil Chemotherapy" Journal of Clinical Oncology, vol. 19, No. 23, Dec. 1, 2001, pp. 4298-4304.
J. Stoehlmacher, et al., "A multivariate analysis of genomic polymorphisms: prediction of clinical outcome to 5-FU/oxaliplatin combination chemotherapy in refractory colorectal cancer" British Journal of Cancer, vol. 91, 2004, pp. 344-354.
David J. Park, et al. "A *Xeroderma Pigmentosum Group* D Gene Polymorphism Predicts Clinical Outcome to Platinum-based Chemotherapy in Patients with Advanced Colorectal Cancer" Cancer Research, vol. 61, Dec. 15, 2001, pp. 8654-8658.
Jan Stoehlmacher, et al., "A Polymorphism of the XRCC1 Gene Predicts for Response to Platinum Based Treatment in Advanced Colorectal Cancer" Anticancer Research, vol. 21, 2001, pp. 3075-3080.
Daniel Fink, et al., "The Role of DNA Mismatch Repair in Platinum Drug Resistance" Cancer Research, vol. 56, Nov. 1, 1996, pp. 4881-4886.
Jan Stoehlmacher, et al., "Association Between Glutathione S-Transferase P1, T1, and M1 Genetic Polymorphism and Survival of Patients With Metastatic Colorectal Cancer" Journal of the National Cancer Institute, vol. 94, No. 12, Jun. 19, 2002, pp. 936-942.
Shuzhong Zhang, et al., "Organic Cation Transporters Are Determinants of Oxaliplatin Cytotoxicity" Cancer Research, vol. 66, No. 17, Sep. 1, 2006, pp. 8847-8857.
Goli Samimi, et al., "Modulation of the Cellular Pharmacology of Cisplatin and Its Analogs by the Copper Exporters ATP7A and ATP7B" Molecular Pharmacology, vol. 66, No. 1, 2004, pp. 25-32.
Goli Samimi, et al., "Increased Expression of the Copper Efflux Transporter ATP7A Mediates Resistance to Cisplatin, Carboplatin, and Oxaliplatin in Ovarian Cancer Cells" Clinical Cancer Research, vol. 10, Jul. 2004, pp. 4661-4669.
Annamaria Ruzzo, et al., "Pharmacogenetic Profiling in Patients with Advanced Colorectal Cancer Treated with First-Line FOLFOX-4 Chemotherapy" Journal of Clinical Oncology, vol. 25, No. 10, Apr. 1, 2007, pp. 1247-1254, and 3262.
Cristine Nadal, et al., "FAS/FAS Ligand Ratio: A Marker of Oxaliplatin-Based Intrinsic and Acquired Resistance in Advanced Colorectal Cancer" Clinical Cancer Research, vol. 11, No. 13, Jul. 1, 2005, pp. 4770-4774.
Gareth J. Griffiths, et al., "Expression of Kinase-defective Mutants of c-Src in Human Metastatic Colon Cancer Cells Decreases Bcl-xL and Increases Oxaliplatin- and Fas-induced Apoptosis" The Journal of Biological Chemistry, vol. 279, No. 44, Oct. 29, 2004, pp. 46113-46121.
Andre B.P. van Kuilenburg, "Dihydropyrimidine dehydrogenase and the efficacy and toxicity of 5-fluorouracil" European Journal of Cancer, vol. 40, 2004, pp. 939-950.
C. Aschele, et al., "Thymidylate Synthase expression as a predictor of clinical response to fluoropyramidine-based chemotherapy in advanced colorectal cancer" Cancer Treatment Reviews, vol. 28, 2002, pp. 27-47.
Sanjay Popoat, et al., "Thymidylate Synthase Expression and Prognosis in Colorectal Cancer: A Systematic Review and Meta-Analysis" Journal of Clinical Oncology, vol. 22, No. 3, Feb. 1, 2004, pp. 529-536.
Chan, et al. J. Clin. Oncol. (2004) 22(15):3052-3060.
Li, et al., Photodiagnosis Photodynamic Ther. (2006) 3:266-271.
Zhang, et al. J. Clin, Oncol. (2005) 23(33):8461-8468.
Pacis, et al. Int. J. Oncology (1995) 7:1349-1354.
Oh, et al. Cancer (2997) 109(3):477-486.
Combined Chinese Office Action and Search Report dated Sep. 24, 2014 in Patent Application No. 201280014973.X with English language translation of summary and English Translation of Category of Cited Documents.
Partial Supplementary European Search Report dated Dec. 1, 2014 in European Patent Application No. 12759998.3.
Abdelhadi Rebbaa, et al., "Expression of Bisecting GlcNAc in Pediatric Brain Tumors and Its Association with Tumor Cell Response to Vinblastine", Clinical Cancer Research, vol. 5, No. 11, XP055137819, (Nov. 1, 1999 ), pp. 3661-3668, Retrieved from the Internet: URL:http://clincancerres.aacrjournals.org/content/5/11/3661.full.pdf#page=1&view=FitH [retrieved on Sep. 2, 2014].
Faqing Tang, et al., "Novel potential markers of nasopharyngeal carcinoma for diagnosis and therapy", Clinical Biochemistry,Elsevier Inc., US, CA, vol. 44, No. 8, XP028209465, (Mar. 4, 2011), pp. 711-718, ISSN: 0009-9120, DOI: 10.1016/J.CLINBIOCHEM.2011. 03. 025 [retrieved on Mar. 12, 2011].
Yuanyan Wei, et al., "Down-regulation of βI, 4GalT V at protein level contributes to arsenic trioxide-induced glioma cell apoptosis", Cancer Letters, New York, NY, US, vol. 267, No. 1, XP022797046 (Aug. 18, 2008), pp. 96-105, ISSN: 0304-3835, DOI:10. 1016/J. CANLET. 2008 03. 019 [retrieved on Apr. 24, 2008].
Combined Chinese Office Action and Search Report dated May 12, 2015 in Patent Application No. 201280014973.X (with partial English language translation and English translation of categories of cited documents).
Akito Nishimuta, et al., "Intracellular metabolite kinetics after 5-FU exposure by CE-TOFMS metabolome analysis" Cancer Research, vol. 68, May 1, 2008, p. 2563.
Alexandra Backshall, et al., "Pharmacometabonomic Profiling as a Predictor of Toxicity in Patients with Inoperable Colorectal Cancer Treated with Capecitabine" Clinical Cancer Research, vol. 17, No. 9, Mar. 17, 2011, pp. 3019-3028.
Peter M. Wilson, et al., "Predictive and Prognostic Markers in Colorectal Cancer" Gastrointestinal Cancer Research, vol. 1, No. 6, 2007, pp. 237-246.
Wendy L. Allen, et al., "Predicting the outcome of chemotherapy for colorectal cancer" Current Opinion in Pharmacology, vol. 6, 2006, pp. 332-336.
Combined Chinese Office Action and Search Report dated Aug. 12, 2016 in Patent Application No. 201280014973.X (with Partial English translation and English translation of categories of cited documents).
European Office Action dated Oct. 17, 2016 in Patent Application No. 16 180 500.7.
Partial European Search Report dated Jan. 26, 2017 in Patent Application No. 16180500.7.
Laurence Gamelin, et al., "Predictive Factors of Oxaliplatin Neurotoxicity: The Involvement of the Oxalate Outcome Pathway", Clin Cancer Res, vol. 13, No. 21, Nov. 1, 2007, pp. 6359-6368.
M. Cobo-Dols, et al., "Changes in the serum amino acids concentrations after first cycle as a factor predictive of tumor response to chemotherapy", Oncologia, vol. 28, No. 7, Jul. 1, 2005, pp. 21-28.

\* cited by examiner

Fig. 1

| Cell lines | IC$_{50}$ ($\mu$M) |
|---|---|
| HT29 | 23.92 ± 9.29 |
| HCT15 | 2.42 ± 0.47 |
| HCT116 | 0.89 ± 0.33 |
| Lovo | 0.72 ± 0.12 |
| LS174T | 5.92 ± 6.12 |
| DLD-1 | 16.95 ± 6.31 |
| WiDr | 17.30 ± 5.24 |
| SW480 | 0.65 ± 0.07 |
| SW620 | 1.12 ± 0.57 |
| SW1116 | 26.42 ± 4.12 |

Mean ± S.D. (n=4 (SW1116, n=3))

Fig. 9

|  | DLD-1 | HCT116 | Ratio (HCT116/DLD-1) |
|---|---|---|---|
| dTMP | 2.15 | 2.77 | 1.29* |
| CMP | 1.73 | 2.59 | 1.50* |
| UMP | 0.85 | 3.67 | 4.30* |
| IMP | 2.08 | 0.54 | 0.26 |
| GMP | 1.44 | 1.95 | 1.36* |
| PRPP | 0.41 | 0.35 | 0.85 |
| CDP | 0.41 | 1.62 | 3.93* |
| UDP | 0.45 | 2.36 | 5.23* |
| dCTP | 1.43 | 2.14 | 1.49* |
| dTTP | 1.17 | 1.10 | 0.94 |
| CTP | 0.87 | 1.76 | 2.03* |
| UTP | 0.83 | 1.46 | 1.76* |
| dATP | 1.14 | 0.93 | 0.81 |
| GTP | 1.07 | 1.73 | 1.61* |
| NAD+ | 1.24 | 1.33 | 1.08 |
| NADH | 1.10 | 1.29 | 1.18 |
| NADP+ | 1.20 | 1.48 | 1.24* |
| ATP+dGTP | 1.07 | 1.73 | 1.61* |

Ratio of intracellular level after 24-hour L-OHP exposure to that of control group in DLD-1 and HCT116
*Considerable intracellular accumulation particularly in HCT116

ATP + dGTP:
Peaks attributed to metabolites of ATP and dGTP were overlapped, due to the exactly same m/z and almost the same capillary electrophoresis flight time of ATP and dGTP

Fig. 12

| | Metabolite | DLD-1 | HCT116 | Ratio (HCT116/DLD-1) |
|---|---|---|---|---|
| Amino acid metabolism | Glu | 1.60 | 2.57 | 1.60 |
| | Arg | 0.91 | 1.79 | 1.97 |
| | Lys | 0.89 | 1.47 | 1.66 |
| | $N^6$-Acetyllysine | 1.19 | 1.87 | 1.57 |
| | N-Acetyl-beta-alanine | 1.53 | 2.33 | 1.52 |
| | N-Acetylornithine | 0 | 1.71 | ∞ |
| | gamma-Glu-Cys | 0 | 2.18 | ∞ |
| | beta-Ala-Lys | 1.03 | 2.83 | 2.74 |
| | Glutathione (GSH) | 11.98 | 2.15 | 0.18 |
| | Glu-Glu | 1.26 | 2.29 | 1.82 |
| | S-Lactoylglutathione | 0.90 | 1.42 | 1.58 |
| | Cadaverine | 0.87 | 3.70 | 4.26 |
| | Cysteic acid | 1.52 | 2.32 | 1.53 |
| | trans-Cinnamic acid | 1.60 | 2.49 | 1.55 |
| | S-Adenosylhomocysteine | 0.86 | 1.34 | 1.56 |
| Nucleotide metabolism | Guanosine | 1.46 | 2.90 | 1.99 |
| Pentose phosphate pathway | 2,3-Diphosphoglyceric acid | 0.79 | 2.13 | 2.69 |
| | Pyruvic acid | 1.50 | 2.30 | 1.54 |
| TCA cycle | Malic acid | 1.19 | 2.26 | 1.90 |
| Polyamine metabolism | N-Acetylputrescine | 1.31 | 2.88 | 2.19 |
| | Spermidine | 0.70 | 1.28 | 1.85 |
| Others | Lauric acid | 1.13 | 1.85 | 1.64 |
| | 6-Phosphogluconic acid | 0.86 | 1.76 | 2.05 |
| | Butyric acid | 2.22 | 1.07 | 0.48 |
| | 4-Methylpyrazole | 1.51 | 0.89 | 0.59 |

Ratio of intracellular level after 24-hour L-OHP exposure to that of control group in DLD-1 and HCT116

Fig. 13

| | Metabolite | DLD-1 | HCT116 | Ratio (HCT116/DLD-1) |
|---|---|---|---|---|
| Amino acid metabolism | Asp | 1.32 | 2.46 | 1.86 |
| | Ser | 5.46 | 3.37 | 0.62 |
| | Ornithine | 1.47 | 2.20 | 1.50 |
| | N-Acetylornithine | 1.03 | 1.76 | 1.71 |
| | 3-Methylhistidine | 1.06 | 0.70 | 0.65 |
| | beta-Ala-Lys | 0.74 | 2.36 | 3.19 |
| | Glutathione (GSH) | 77.77 | 2.59 | 0.03 |
| | Glu-Glu | 0.94 | 1.58 | 1.69 |
| | Cysteine-glutathione | 0.09 | 0.25 | 2.91 |
| | Cadaverine | 0.73 | 0.47 | 0.64 |
| | 2-Aminoadipic acid | 0.97 | 1.48 | 1.52 |
| | gamma-Aminobutyric acid | 0.68 | 1.56 | 2.29 |
| | S-Adenosylhomocysteine | 0.91 | 1.84 | 2.02 |
| Nucleotide metabolism | Guanosine | 1.27 | 2.03 | 1.61 |
| | CMP | 1.08 | 2.30 | 2.13 |
| | UMP | 0.70 | 2.06 | 2.96 |
| | 1-Methyladenosine | 0.94 | 1.95 | 2.08 |
| | UDP | 0.68 | 1.55 | 2.27 |
| | CTP | 0.67 | 1.45 | 2.17 |
| | Adenosine | 2.04 | 0.96 | 0.47 |
| Pentose phosphate pathway | Sedoheptulose 7-phosphate | 1.00 | 2.21 | 2.20 |
| | PRPP | 0.77 | 0.28 | 0.36 |
| Glycolysis | Dihydroxyacetone phosphate | 0.56 | 1.66 | 2.95 |
| | 2,3-Diphosphoglyceric acid | 0.61 | 1.15 | 1.89 |
| | Pyruvic acid | 0.95 | 1.59 | 1.67 |
| TCA cycle | Malic acid | 0.98 | 1.75 | 1.79 |
| Polyamine metabolism | $N^1$-Acetylspermine | 1.54 | 2.68 | 1.74 |
| | N-Acetylputrescine | 0.36 | 0.76 | 2.14 |
| | $N^8$-Acetylspermidine | 0.51 | 1.49 | 2.93 |
| | Putrescine | 0.23 | 0.75 | 3.20 |
| | Spermidine | 0.46 | 1.07 | 2.31 |
| Others | Isobutylamine | 1.06 | 1.63 | 1.53 |
| | Glycolic acid | 0.96 | 1.49 | 1.55 |
| | 6-Phosphogluconic acid | 0.53 | 1.08 | 2.03 |
| | 4-Methylpyrazole | 1.28 | 0.69 | 0.54 |
| | NADH | 0.39 | 0.67 | 1.70 |
| | $NAD^+$ | 0.25 | 0.51 | 2.03 |

Ratio of intracellular level after 24-hour 5-FU exposure to that of control group in DLD-1 and HCT116

METHOD FOR DETERMINING SENSITIVITY TO FLUOROURACIL IN A SUBJECT HAVING COLORECTAL CANCER

CROSS-REFERENCE TO RELATED APPLICATIONS

This application is a divisional of U.S. application Ser. No. 14/007,145 filed Dec. 5, 2013, now U.S. Pat. No. 9,797,884, which is a National Stage application of PCT/JP 2012/054633 filed Feb. 24, 2012and claims the benefit of JP 2011-065993 filed Mar. 24, 2011.

TECHNICAL FIELD

The present invention relates to a marker for use in determination of the sensitivity of a cancer patient to an anti-cancer agent, which marker can determine whether or not the cancer of the patient has a therapeutic response to the anti-cancer agent, and to application of the marker.

BACKGROUND ART

Anti-cancer agents have various types such as an alkylating agent, a platinum agent, an antimetabolite, an antitumor antibiotic, and an antitumor plant alkaloid. These anti-cancer agents are effective for some cancers but not effective for other cancers. Even when an anti-cancer agent is confirmed to be effective for a certain cancer, the anti-cancer agent is effective for some patients and not effective for other patients, leading to interindividual differences. Whether or not a cancer of a specific patient has response to an anti-cancer agent is designated as sensitivity to the anti-cancer agent.

Oxaliplatin, (SP-4-2)-[(1R,2R)-cyclohexane-1,2-diamine-κN,κN'] [ethanedioato(2-)-κO$^1$, κO$^2$]platinum (IUPAC), is a third-generation platinum-based complex anti-cancer agent. Similar to precedent drugs (cisplatin (CDDP) and carboplatin (CBDCA)), the action mechanism thereof is thought to be based on inhibition of DNA synthesis and/or protein synthesis via cross-linking with DNA bases. Oxaliplatin (L-OHP) exhibits anti-tumor effect on colorectal cancer, to which CDDP or CBDCA is ineffective, and shows a different spectrum of anti-tumor activity from that of a precedent platinum-based complex anti-cancer agent. In the United States of America, oxaliplatin for use in combination with fluorouracil (5-FU) and levofolinate (LV) was approved as a first line therapy for metastatic colorectal cancer in January, 2004. In Japan, oxaliplatin was listed in the National Health Insurance (NHI) price list in the case of combination use thereof with continuous infusional fluorouracil and levofolinate (FOLFOX4 regimen) for "advanced/recurrent colorectal cancer not amenable to curative surgical resection" in April, 2005. Until the early 1990's, 5-FU/LV regimen to advanced/recurrent colorectal cancer has provided a survival of 10 to 12 months. In contrast, a FOLFOX regimen combined with oxaliplatin results in a prolonged survival of 19.5 months (about twice the survival time). In August, 2009, an indication of oxaliplatin combined with continuous infusional 5-FU/LV to "postoperative adjuvant chemotherapy for colon cancer" was added to efficacy and effectiveness. Thus, oxaliplatin is a promising drug having an efficacy in an increased number of colorectal cancer patients.

However, the response rate of FOLFOX regimen against advanced/recurrent colorectal cancer is still as low as about 50%. In other words, about half of the treated patients achieve no effects. During administration of oxaliplatin, peripheral neuropathy frequently occurs in addition to neutropenia. Although not being fatal, these adverse events are factors which make continuation of the therapy difficult. Therefore, if a patient who is expected to achieve the response (i.e., a responder) and a patient who is not expected to achieve the response (i.e., a non-responder) can be predicted and diagnosed before start of the treatment, a chemotherapy ensuring high effectiveness and high safety can be established. Furthermore, since the therapy schedule of cancer chemotherapy generally requires a long period of time, continuous monitoring of sensitivity of a target patient to a target anti-cancer agent during the therapy can determine whether or not the therapy should be continued. Thus, such monitoring is thought to be meritorious from the viewpoints of reduction or mitigation of the burden on patients and adverse events, leading to reduction in medical cost. Therefore, there is keen demand for establishment of a biomarker that can predict therapeutic response, for the purpose of predicting therapeutic response of individual patients and selecting an appropriate treatment; i.e., for realizing "personalized medicine."

As factors related with the therapeutic response of patients to oxaliplatin, the followings may be mainly involved:

1) enhancement of the ability of excising and repairing DNA damaged by oxaliplatin;

2) inactivation (detoxification) of oxaliplatin (active form) in cells; and 3) reduction in accumulation amount of oxaliplatin in cells. In the oxaliplatin and 5-FU combination therapy for colorectal cancer patients, the therapeutic response and prognosis-predicting factor are now under study on the basis of 1) to 3).

Regarding 1), the excision repair cross-complementing group 1 (ERCC1) gene expression level in tumor cells is reported to serve as a prognosis factor, the ERCC1 playing an important role in nucleotide excision repair (NER) (Non-Patent Document 1). Patients having a C/C homozygote of C118T (a type of single nucleotide polymorphism (SNP) of ERCC1) exhibit a survival longer than that of patients having at least one T allele (Non-Patent Document 2). In Xeroderma pigmentosum D (XPD, also known as ERCC2), a genetic polymorphism involving Lys751Gln amino acid mutation is reported to relate to percent tumor reduction and survival (Non-Patent Documents 2 and 3). In base excision repair (BER), there has been reported a relationship between the tumor reduction effect and a genetic polymorphism involving Arg399Gln amino acid mutation in X-ray repair cross-complementing group 1 (XRCC1) encoding a protein relating to effective repair of DNA single strand breakage caused by exposure to an alkylating agent or the like (Non-Patent Document 4). However, further analysis of the same patients has revealed that the genetic polymorphism does not affect the clinical prognosis (Non-Patent Document 2). DNA mismatch repair (MMR) is thought to relate to lowering sensitivity to cisplatin. However, in vitro studies have revealed that MMR does not involve repair of DNA damaged by oxaliplatin (Non-Patent Document 5).

Regarding 2), glutathione-S-transferase (GST) is an enzyme which catalyzes phase II reaction in the detoxification and metabolism. GST catalyzes formation of a conjugation of a DNA-platinum adduct and glutathione, to thereby inactivate a drug. Among GST subtypes, GSTP1 has a high expression level in colorectal cancer, and a genetic polymorphism involving Ile105Val amino acid mutation relates to survival (median survival: Ile/Ile 7.9 months, Ile/Val 13.3 months, Val/Val 24.9 months) (Non-Patent Document 6).

Regarding 3), studies employing cultured cells have revealed that organic cation transporters (OCTs) relate to transportation of oxaliplatin into cells and sensitivity to oxaliplatin (Non-Patent Document 7). A relationship between copper- and heavy-metal-transporters such as ATP7A and ATP7B and sensitivity has also been reported (Non-Patent Documents 8 and 9). However, the relationship between expression of these transporters and therapeutic response to oxaliplatin has not been clinically elucidated.

Recent clinical studies for advanced colorectal cancer patients having received FOLFOX regimen have revealed that a genetic polymorphism of ERCC1 (Asn118Asn) and that of XPD (Lys751Gln) independently relate to progression-free survival (PFS), and that a genetic polymorphism of GSTP1 (Ile105Val) does not relate to PFS but tends to have a relationship with oxaliplatin-induced neurotoxicity (Non-Patent Document 10).

In vitro studies have revealed a number of resistance-related factors of cisplatin (a precedent platinum-based complex drug), and the relationship between oxaliplatin and apoptosis-related factors such as FAS/FASL and Bcl-xL have been reported (Non-Patent Documents 11 and 12). However, oxaliplatin exhibits a therapeutic response differing from that of cisplatin, depending on the type of cancer. In addition, there has not been substantially elucidated the cell response of cancer cells with respect to a platinum-DNA adduct, which exerts cytotoxic activity of oxaliplatin. Thus, there has been established no definite biomarker which can predict the therapeutic response to chemotherapy employing oxaliplatin.

Meanwhile, fluorouracil is a fluoro-pyrimidine anti-cancer agent developed in 1957 and even now serves as a basic drug for use in the chemotherapy of gastrointestinal cancer. When incorporated into cancer cells, fluorouracil exerts cytotoxic effect through a principle action mechanism of DNA synthesis inhibition induced by inhibition of thymidylate synthase (TS) by an active metabolite, fluorodeoxyuridine-5'-monophosphate (FdUMP), and another mechanism of RNA function inhibition by an active metabolite, 5-fluorouridine triphosphate (FUTP).

Hitherto, many studies have been conducted to predict therapeutic response to fluoro-pyrimidine anti-cancer agents. In particular, many studies have been focused on dihydropyrimidine dehydrogenase (DPD), which is a fluorouracil degrading enzyme, and thymidylate synthase (TS), which is a target enzyme of an active metabolite. A tumor in which DPD, a rate-limiting enzyme in the catabolism of fluorouracil, is highly expressed is reported to have resistance to fluorouracil (Non-Patent Document 13), but a limited number of studies have been conducted with clinical specimens. The TS expression level is reported to be a possible factor that determines the therapeutic effect by a fluoro-pyrimidine anti-cancer agent, even when the expression level is determined through any assay method such as the enzymatic activity method, protein level assay, or RNA level assay (Non-Patent Documents 14 and 15). However, the above-obtained results are not completely the same, and there has been known no definite biomarker which can predict the therapeutic response to fluorouracil in an early treatment stage.

PRIOR ART DOCUMENT

Non-Patent Document

Non-Patent Document 1: J. Clin. Oncol. 19, 4298-4304 (2001)

Non-Patent Document 2: Br. J. Cancer 91, 344-354 (2004)
Non-Patent Document 3: Cancer Res. 61, 8654-8658 (2001)
Non-Patent Document 4: Anticancer Res. 21, 3075-3079 (2001)
Non-Patent Document 5: Cancer Res. 56, 4881-4886 (1996)
Non-Patent Document 6: J. Natl. Cancer Inst. 94, 936-942 (2002)
Non-Patent Document 7: Cancer Res. 66, 8847-8857 (2006)
Non-Patent Document 8: Mol. Pharmacol. 66, 25-32 (2004)
Non-Patent Document 9: Clin. Cancer Res. 10, 4661-4669 (2004)
Non-Patent Document 10: J. Clin. Oncol. 25, 1247-1254 (2007)
Non-Patent Document 11: Clin. Cancer Res. 11, 4770-4774 (2005)
Non-Patent Document 12: J. Biol. Chem. 279, 46113-46121 (2004)
Non-Patent Document 13: European Journal of Cancer 2004; 40: 939-950
Non-Patent Document 14: Cancer Treatment Reviews 2002; 28: 27-47
Non-Patent Document 15: J. Clin. Oncol. 2004; 22: 529-536

SUMMARY OF THE INVENTION

Problems to be Solved by the Invention

An object of the present invention is to provide a marker for determining sensitivity of a patient to an anti-cancer agent, which marker can determine whether or not the patient has a therapeutic response to the anti-cancer agent. Another object is to provide novel cancer therapeutic means employing the marker.

Means for Solving the Problems

In order to attain the aforementioned objects, the present inventors have searched for a marker for determining sensitivity to an anti-cancer agent by culturing human cancer cells of 10 strains, and analyzing the intracellular metabolites by means of a capillary electrophoresis/time-of-flight mass spectrometer (CE-TOFMS). As a result, the inventors have found metabolites each exhibiting a difference in level between oxaliplatin (also called L-OHP)-low-sensitivity cells and L-OHP-high-sensitivity cells, the metabolites being N-acetylglucosamine, amino-acid-metabolism-related substances (N-acetylaspartic acid, N-acetyl-β-alanine, asparagine (Asn), arginine (Arg), and ornithine), a polyamine-metabolism-related substance (spermidine), and substances in the glycolytic pathway (3-phosphoglycerate and fructose-1,6-diphosphate). The present inventors have also searched for a marker for determining sensitivity to an anti-cancer agent by culturing human cancer cells of several strains, and comprehensively analyzing the intracellular metabolism behavior after exposure to L-OHP by means of a CE-TOFMS. As a result, the inventors have found peaks attributed to substances which exhibit, after exposure to L-OHP, a considerable rise in intracellular level in L-OHP-high-sensitivity cells, the substances being amino-acid-metabolism-related substances (β-alanine (β-Ala), asparagine, glutamic acid (Glu), Arg, lysine (Lys), $N^6$-acetyllysine, N-acetyl-β-alanine, N-acetylornithine, γ-Glu-Cys, β-Ala-Lys, Glu-Glu, S-lactoylglutathione, cadaverine, cysteic acid, trans-cinnamic acid, and S-adenosylhomocysteine), polyamine-metabolism-related substances (putrescine, $N^1$-acetylspermine, $N^8$-acetylspermidine, spermine, spermidine, and N-acetylputrescine), nucleic-acid-metabolism-related substances (dTMP, CMP, UMP, GMP, CDP, UDP, dCTP, CTP, UTP, GTP, $NADP^+$, ATP and/or dGTP, and guanosine), substances in the pentose phosphate pathway (2,3-diphosphoglyceric acid and pyruvic acid), a substance in the TCA cycle (malic acid), lauric acid, and 6-phosphogluconic acid. Further, the inventors have found peaks attributed to substances which exhibit, after exposure to L-OHP, a considerable rise in intracellular level in L-OHP-low-sensitivity cells, the substances being an amino-acid-metabolism-related substances (glutathione (GSH)), butyric acid, and 4-methylpyrazole. Also, the inventors have found peaks attributed to a substance which exhibits, after exposure to L-OHP, a considerable drop in intracellular level in L-OHP-high-sensitivity cells, the substance being a nucleic-acid-metabolism-related substance (IMP).

Similarly, the present inventors also have searched for a marker for determining sensitivity to an anti-cancer agent by culturing human cancer cells of several strains, and comprehensively analyzing the intracellular metabolism behavior after exposure to fluorouracil (also called 5-FU) by means of a CE-TOFMS. As a result, the inventors have found peaks attributed to substances which exhibit, after exposure to 5-FU, a considerable rise in intracellular level in 5-FU-high-sensitivity cells, the substances being amino-acid-metabolism-related substances (aspartic acid (Asp), ornithine, N-acetylornithine, β-Ala-Lys, Glu-Glu, 2-aminoadipic acid, γ-aminobutyric acid, and S-adenosylhomocysteine), nucleic-acid-metabolism-related substances (guanosine, CMP, UMP, 1-methyladenosine, UDP, and CTP), a substance in the pentose phosphate pathway (sedoheptulose 7-phosphate), substances in the glycolytic pathway (dihydroxyacetone phosphate and pyruvic acid), a substance in the TCA cycle (malic acid), a polyamine-metabolism-related substance ($N^1$-acetylspermine), isobutylamine, and glycolic acid. The inventors further have found peaks attributed to substances which exhibit, after exposure to 5-FU, a considerable rise in intracellular level in 5-FU-low-sensitivity cells, the substances being amino-acid-metabolism-related substances (serine (Ser) and glutathione (GSH)) and a nucleic-acid-metabolism-related substance (adenosine). The inventors further have found peaks attributed to substances which exhibit, after exposure to 5-FU, a considerable drop in intracellular level in 5-FU-high-sensitivity cells, the substances being amino-acid-metabolism-related substances (3-methylhistidine and cadaverine), a substance in the pentose phosphate pathway (PRPP), and 4-methylpyrazole. The inventors further have found peaks attributed to substances which exhibit, after exposure to 5-FU, a considerable drop in intracellular level in 5-FU-low-sensitivity cells, the substances being an amino-acid-metabolism-related substance (cysteine-glutathione), a substance in the glycolytic pathway (2,3-diphosphoglyceric acid), polyamine-metabolism-related substances (N-acetylputrescine, $N^8$-acetylspermidine, putrescine, and spermidine), 6-phosphogluconic acid, NADH, and $NAD^+$.

On the basis of these findings, the inventors have carried out further studies, and have found that whether or not a cancer of a target cancer patient has a sensitivity to an anti-cancer agent can be determined through measuring the levels of any of the metabolites contained in a biological sample derived from the cancer patient as an index; that screening of an anti-cancer agent sensitivity enhancer can be accomplished through employment of the levels (or variation in level) of any of the metabolites as an index; and that the therapeutic effect of the relevant anti-cancer agent can be drastically enhanced by use, in combination, of the anti-cancer agent sensitivity enhancer and the anti-cancer agent which is a sensitivity enhancement target of the enhancer. The present invention has been accomplished on the basis of these findings.

Accordingly, the present invention provides a marker for determining sensitivity to an anti-cancer agent, the marker comprising one or more substances selected from the group consisting of N-acetylglucosamine, an amino-acid-metabolism-related substance, a nucleic-acid-metabolism-related substance, a substance in the pentose phosphate pathway, a substance in the glycolytic pathway, a substance in the TCA cycle, a polyamine-metabolism-related substance, lauric acid, 6-phosphogluconic acid, butyric acid, 4-methylpyrazole, isobutylamine, glycolic acid, NADH, $NAD^+$, and a substance involved in the metabolism of any of these substances.

The present invention also provides a marker for determining sensitivity to an anti-cancer agent selected from L-OHP, 5-FU, and a salt of any one of these, the marker comprising one or more substances selected from the group consisting of Asn, γ-Glu-Cys, glutathione (GSH), S-adenosylhomocysteine, Asp, γ-aminobutyric acid, 1-methyladenosine, spermine, spermidine, and a substance involved in the metabolism of any of these substances.

The present invention also provides a method for determining sensitivity of a subject to an anti-cancer agent, the method comprising measuring the level of any of these substances in a specimen derived from the subject.

The present invention also provides a kit for carrying out the method for determining sensitivity of a subject to an anti-cancer agent, the kit comprising a protocol for measuring the level of any of these substances in a specimen derived from the subject.

The present invention also provides a screening method for an anti-cancer agent sensitivity enhancer, the method comprising employing variation in level of any of these substances as an index.

The present invention also provides an anti-cancer agent sensitivity enhancer selected through the screening method.

The present invention also provides a composition for cancer therapy comprising, in combination, the anti-cancer agent sensitivity enhancer and an anti-cancer agent which is a sensitivity enhancement target of the enhancer.

Effects of the Invention

According to the marker for determining sensitivity to anti-cancer agent of the present invention, the therapeutic response of a patient to an anti-cancer agent can be accurately determined before administration of the anti-cancer agent or in an early stage after start of the administration of the anti-cancer agent. As a result, an anti-cancer agent having higher therapeutic effect can be selected, and progression of cancer and aggravation of adverse events, which would otherwise result from continuous administration of an anti-cancer agent exerting no expected therapeutic effect, can be prevented. Thus, reductions can be expected in the burden on the patients and medical cost. In addition, when the marker of the present invention is used, a drug which can promote anti-cancer agent sensitivity can be selected through screening. Thus, through employment, in combination, of the target anti-cancer agent and an anti-cancer agent sensitivity enhancer to the anti-cancer agent, the expected cancer therapeutic effect can be drastically enhanced. The assay reagent for measuring the marker for determining sensitivity to an anti-cancer agent of the present invention is useful as a reagent for determining sensitivity to an anti-cancer agent.

BRIEF DESCRIPTION OF THE DRAWINGS

FIG. 1 A table showing L-OHP sensitivity of 10 human colorectal cancer cell lines.

FIG. 9 A table showing intracellular nucleic-acid-metabolism-related substance levels in DLD-1 cells and in HCT 116 cells, after 24-hour exposure to L-OHP.

FIG. 12 A table showing intracellular metabolite levels in DLD-1 cells and in HCT 116 cells, after 24-hour exposure to L-OHP.

FIG. 13 A table showing intracellular metabolite levels in DLD-1 cells and in HCT 116 cells, after 24-hour exposure to 5-FU.

MODES FOR CARRYING OUT THE INVENTION

Figure 2:
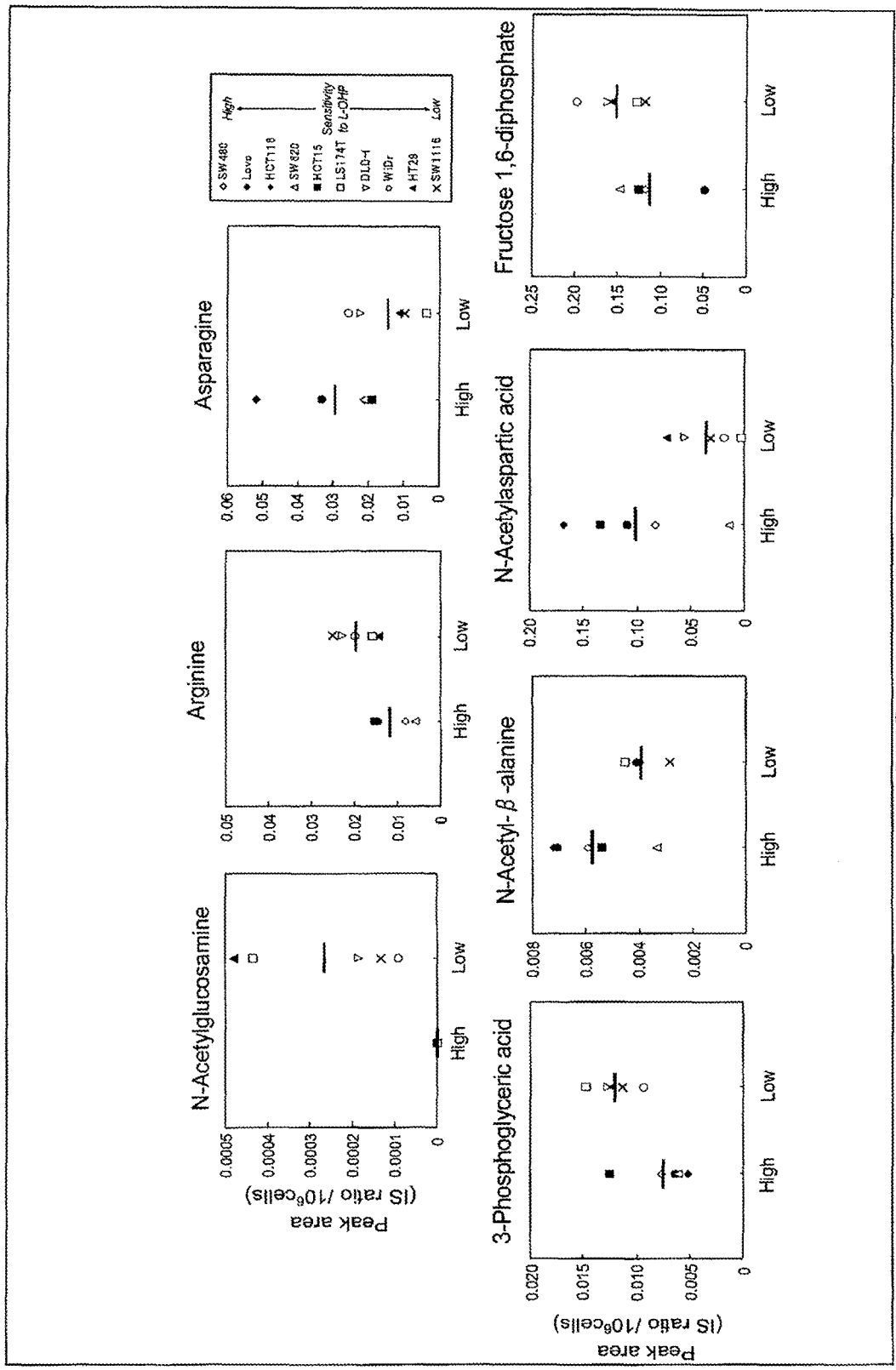
FIG. 2 Graphs showing intracellular substance levels in L-OHP-low-sensitivity cells and in L-OHP-high-sensitivity cells in a steady state (before drug treatment) (substances: N-acetylglucosamine, arginine, asparagine, 3-phosphoglycerate, N-acetyl-β-alanine, N-acetylaspartic acid, and fructose-1,6-diphosphate).
Figure 3:
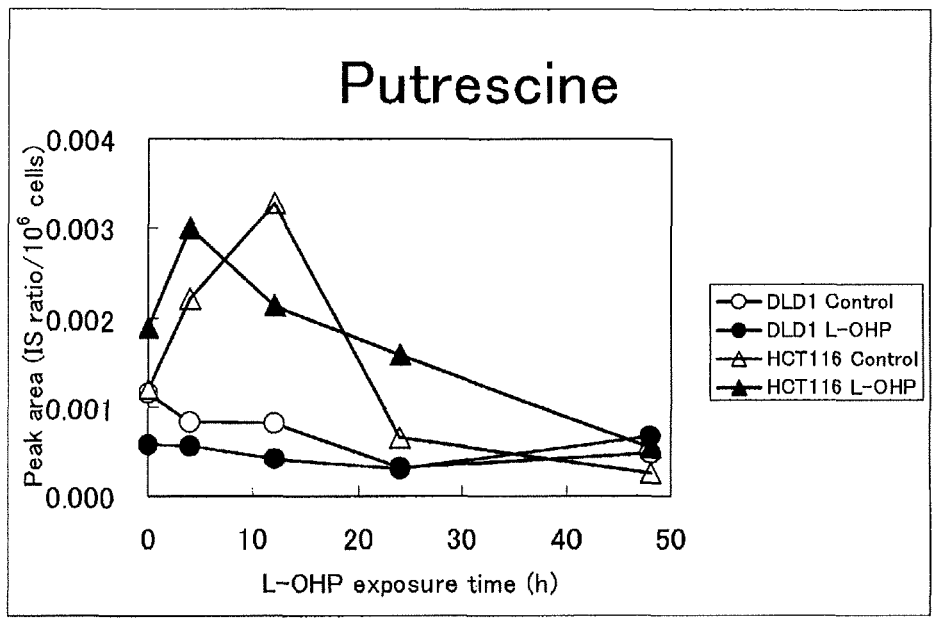
FIG. 3 A graph showing a time-dependent profile of intracellular putrescine level in DLD-1 cells and that in HCT 116 cells under exposure to L-OHP.
Figure 4:
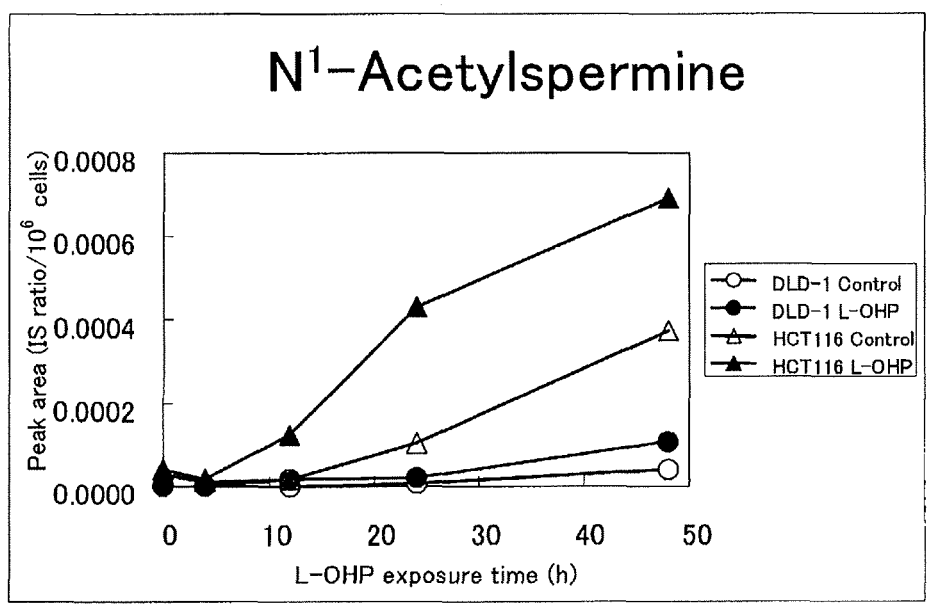
FIG. 4 A graph showing a time-dependent profile of intracellular $N^1$-acetylspermine level in DLD-1 cells and that in HCT 116 cells under exposure to L-OHP.
Figure 5:
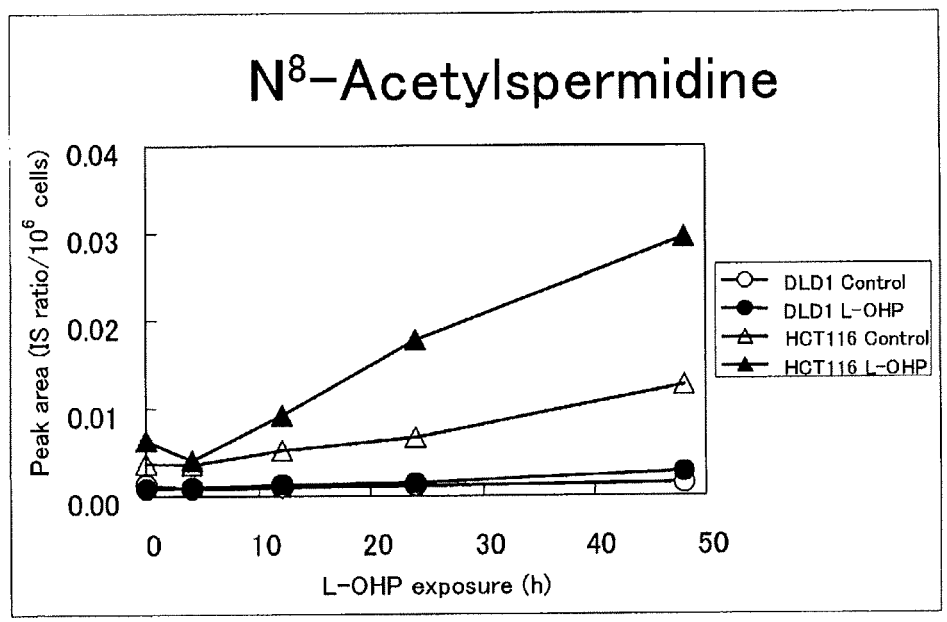
FIG. 5 A graph showing a time-dependent profile of intracellular $N^8$-acetylspermidine level in DLD-1 cells and that in HCT 116 cells under exposure to L-OHP.
Figure 6:
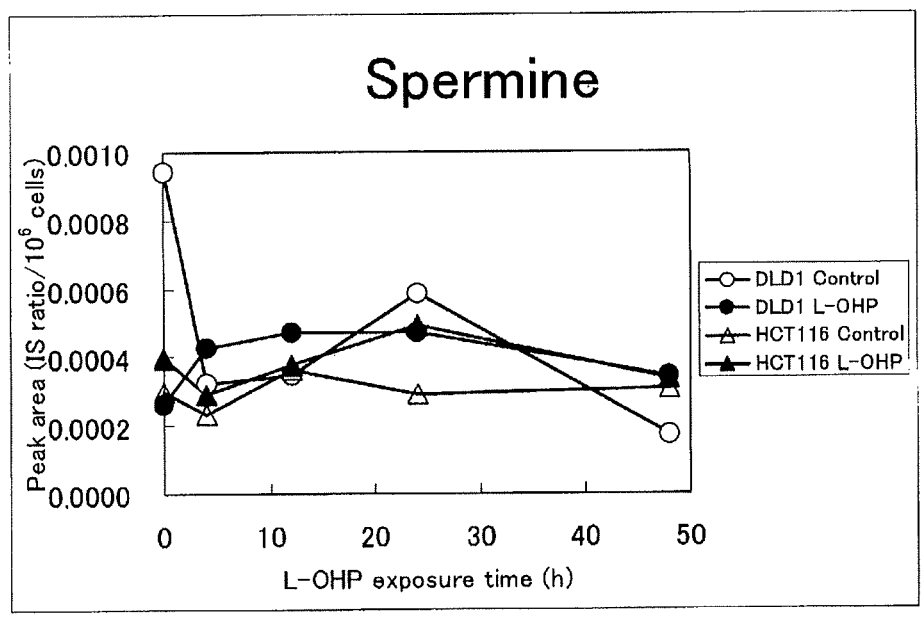
FIG. 6 A graph showing a time-dependent profile of intracellular spermine level in DLD-1 cells and that in HCT 116 cells under exposure to L-OHP.
Figure 7:
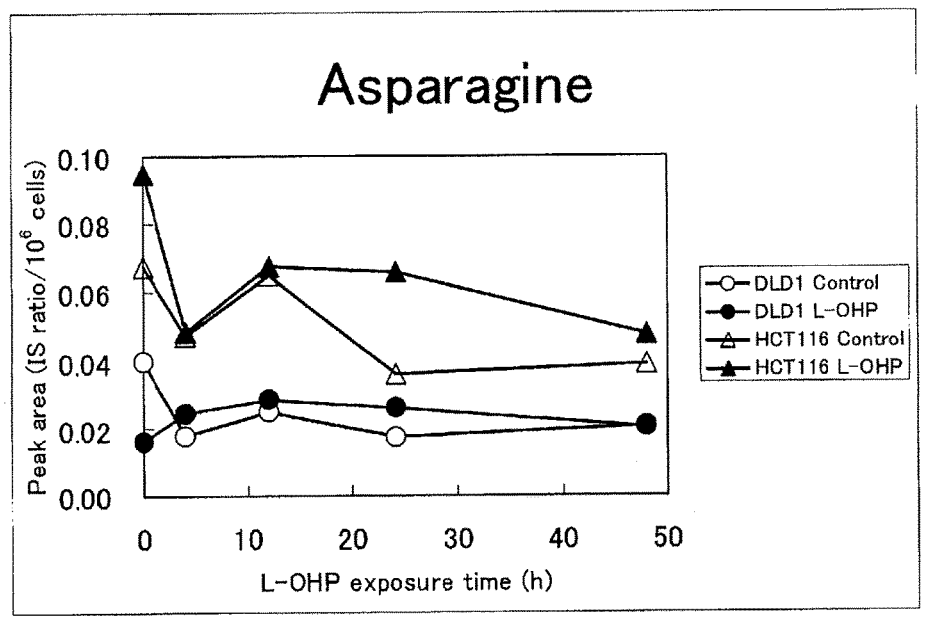
FIG. 7 A graph showing a time-dependent profile of intracellular asparagine level in DLD-1 cells and that in HCT 116 cells under exposure to L-OHP.
Figure 8:
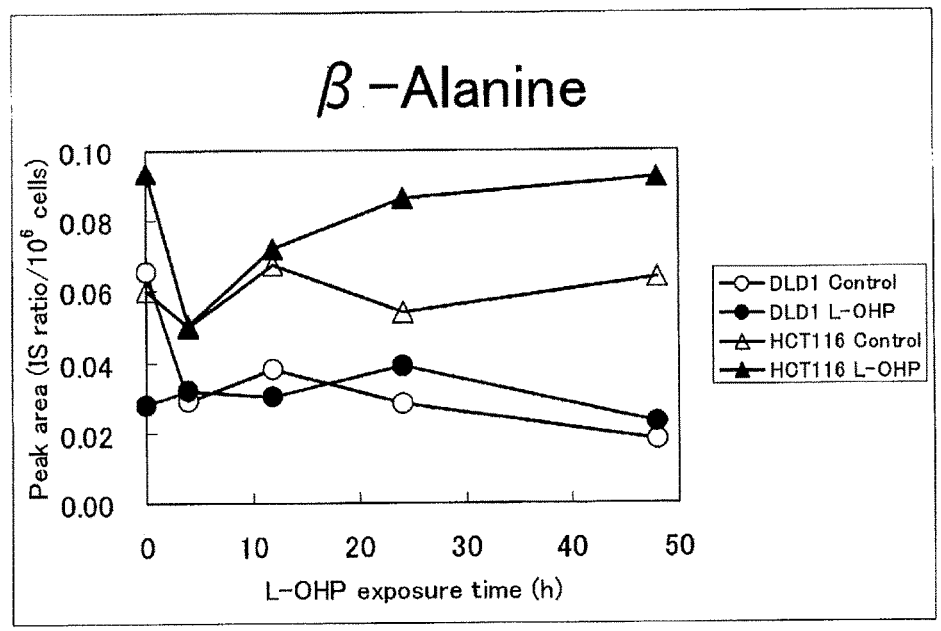
FIG. 8 A graph showing a time-dependent profile of intracellular β-alanine level in DLD-1 cells and that in HCT 116 cells under exposure to L-OHP.

The marker for determining sensitivity to an anti-cancer agent of the present invention is any of the substances selected from the group consisting of N-acetylglucosamine, an amino-acid-metabolism-related substance, a nucleic-acid-metabolism-related substance, a substance in the pentose phosphate pathway, a substance in the glycolytic pathway, a substance in the TCA cycle, a polyamine-metabolism-related substance, lauric acid, 6-phosphogluconic acid, butyric acid, 4-methylpyrazole, isobutylamine, glycolic acid, NADH, $NAD^+$, and a substance involved in the metabolism of any of these substances. The marker for determining sensitivity to an anti-cancer agent also encompasses all the metabolism-related substances that can vary the level of any of these substances.

Examples of such metabolism-related substances include a substance which promotes metabolism to these substances, a substance which inhibits the metabolism, a substance which promotes metabolism from these substances, and a substance which inhibits the metabolism.

One member of the marker for determining sensitivity to an anti-cancer agent of the present invention is N-acetylglucosamine or a substance involved in the metabolism of N-acetylglucosamine (also called an N-acetylglucosamine-metabolism-related substance). The substance encompasses N-acetylglucosamine and all the substances that can vary the N-acetylglucosamine level in the metabolism thereof. Examples of such metabolism-related substances include a substance which promotes metabolism to N-acetylglucosamine, a substance which inhibits metabolism to N-acetylglucosamine, a substance which promotes metabolism from N-acetylglucosamine, and a substance which inhibits metabolism from N-acetylglucosamine. Of these, N-acetylglucosamine is particularly preferred as a marker for determining sensitivity to L-OHP.

Another member of the marker for determining sensitivity to an anti-cancer agent of the present invention is a substance involved in amino acid metabolism (also called an amino-acid-metabolism-related substance). The substance encompasses all the substances that can vary the amino-acid-metabolism-related substance level. Examples of such metabolism-related substances include a substance which promotes metabolism to the amino-acid-metabolism-related substance, a substance which inhibits metabolism to the amino-acid-metabolism-related substance, a substance which promotes metabolism from the amino-acid-metabolism-related substance, and a substance which inhibits metabolism from the amino-acid-metabolism-related substance. Of these, Arg, Asn, N-acetyl-β-alanine, N-acetylaspartic acid, β-alanine, ornithine, Glu, Lys, $N^6$-acetyllysine, N-acetylornithine, γ-Glu-Cys, β-Ala-Lys, glutathione (GSH), Glu-Glu, S-lactoylglutathione, cadaverine, cysteic acid, trans-cinnamic acid, and S-adenosylhomocysteine are particularly preferred as markers for determining sensitivity to L-OHP. Also, Asp, ornithine, N-acetylornithine, β-Ala-Lys, Glu-Glu, 2-aminoadipic acid, γ-aminobutyric acid (GABA), S-adenosylhomocysteine, Ser, glutathione (GSH), 3-methylhistidine, cadaverine, and cysteine-glutathione are particularly preferred as markers for determining sensitivity to 5-FU.

Another member of the marker for determining sensitivity to an anti-cancer agent of the present invention is a substance involved in nucleic acid metabolism (also called a nucleic-acid-metabolism-related substance). The substance encompasses all the substances that can vary the nucleic-acid-metabolism-related substance level. Examples of such metabolism-related substances include a substance which promotes metabolism to the nucleic-acid-metabolism-related substance, a substance which inhibits metabolism to the nucleic-acid-metabolism-related substance, a substance which promotes metabolism from the nucleic-acid-metabolism-related substance, and a substance which inhibits metabolism from the nucleic-acid-metabolism-related substance. Of these, guanosine, dTMP, CMP, UMP, IMP, GMP, CDP, UDP, dCTP, CTP, UTP, GTP, $NADP^+$, ATP and/or dGTP are preferred as markers for determining sensitivity to L-OHP, with UMP and UDP being particularly preferred. Also, guanosine, CMP, UMP, 1-methyladenosine, UDP, CTP, and adenosine are particularly preferred as markers for determining sensitivity to 5-FU.

Another member of the marker for determining sensitivity to an anti-cancer agent of the present invention is a substance involved in the pentose phosphate pathway (also called a substance in the pentose phosphate pathway). The substance encompasses all the substances that can vary the substance level in the pentose phosphate pathway. Examples of such substances include a substance which promotes metabolism to a substance in the pentose phosphate pathway, a substance which inhibits metabolism to a substance in the pentose phosphate pathway, a substance which promotes metabolism from a substance in the pentose phosphate pathway, and a substance which inhibits metabolism from a substance in the pentose phosphate pathway. Of these, 2,3-diphosphoglyceric acid and pyruvic acid are particularly preferred as markers for determining sensitivity to L-OHP. Also, sedoheptulose 7-phosphate and PRPP are particularly preferred as markers for determining sensitivity to 5-FU.

Another member of the marker for determining sensitivity to an anti-cancer agent of the present invention is a substance involved in glycolytic pathway (also called a substance in the glycolytic pathway). The substance encompasses all the substances that can vary the substance level in the glycolytic pathway. Examples of such substances include a substance which promotes metabolism to a substance in the glycolytic pathway, a substance which inhibits metabolism to a substance in the glycolytic pathway, a substance which promotes metabolism from a substance in the glycolytic pathway, and a substance which inhibits metabolism from a substance in the glycolytic pathway. Of these, 3-phosphoglycerate and fructose-1,6-diphosphate are particularly preferred as markers for determining sensitivity to L-OHP. Also, dihydroxyacetone phosphate, 2,3-diphosphoglyceric acid, and pyruvic acid are particularly preferred as markers for determining sensitivity to 5-FU.

Another member of the marker for determining sensitivity to an anti-cancer agent of the present invention is a substance involved in TCA cycle (also called a substance in the TCA cycle). The substance encompasses all the substances that can vary the substance level in the TCA cycle. Examples of such substances include a substance which promotes metabolism to a substance in the TCA cycle, a substance which inhibits metabolism to a substance in the TCA cycle, a substance which promotes metabolism from a substance in the TCA cycle, and a substance which inhibits metabolism from a substance in the TCA cycle. Of these, malic acid is particularly preferred as a marker for determining sensitivity to L-OHP. Malic acid is also particularly preferred as a marker for determining sensitivity to 5-FU.

Another member of the marker for determining sensitivity to an anti-cancer agent of the present invention is a substance involved in polyamine metabolism (also called a polyamine-metabolism-related substance). The substance encompasses all the substances that can vary the polyamine-metabolism-related substance level. Examples of such metabolism-related substances include a substance which promotes metabolism to a polyamine-metabolism-related substance, a substance which inhibits metabolism to a polyamine-metabolism-related substance, a substance which promotes metabolism from a polyamine-metabolism-related substance, and a substance which inhibits metabolism from a polyamine-metabolism-related substance. Of these, putrescine, $N^1$-acetylspermine, $N^8$-acetylspermidine, spermine, spermidine, and N-acetylputrescine are particularly preferred as markers for determining sensitivity to L-OHP. Also, putrescine, $N^1$-acetylspermine, $N^8$-acetylspermidine, spermidine, and N-acetylputrescine are particularly preferred as markers for determining sensitivity to 5-FU.

Another member of the marker for determining sensitivity to an anti-cancer agent of the present invention is lauric acid or a substance involved in lauric acid metabolism (also called a lauric-acid-metabolism-related substance). The substance encompasses lauric acid and all the substances that can vary the lauric acid level in the metabolism thereof. Examples of such metabolism-related substances include a substance which promotes metabolism to lauric acid, a substance which inhibits metabolism to lauric acid, a substance which promotes metabolism from lauric acid, and a substance which inhibits metabolism from lauric acid. Of these, lauric acid is particularly preferred as a marker for determining sensitivity to L-OHP.

Another member of the marker for determining sensitivity to an anti-cancer agent of the present invention is 6-phosphogluconic acid or a substance involved in 6-phosphogluconic acid metabolism (also called a 6-phosphogluconic-acid-metabolism-related substance). The substance encompasses 6-phosphogluconic acid and all the substances that can vary the 6-phosphogluconic acid level in the metabolism thereof. Examples of such metabolism-related substances include a substance which promotes metabolism to 6-phosphogluconic acid, a substance which inhibits metabolism to 6-phosphogluconic acid, a substance which promotes metabolism from 6-phosphogluconic acid, and a substance which inhibits metabolism from 6-phosphogluconic acid. Of these, 6-phosphogluconic acid is particularly preferred as a marker for determining sensitivity to L-OHP and as a marker for determining sensitivity to 5-FU.

Another member of the marker for determining sensitivity to an anti-cancer agent of the present invention is butyric acid or a substance involved in butyric acid metabolism (also called a butyric-acid-metabolism-related substance). The substance encompasses butyric acid and all the substances that can vary the butyric acid level in the metabolism thereof. Examples of such metabolism-related substances include a substance which promotes metabolism to butyric acid, a substance which inhibits metabolism to butyric acid, a substance which promotes metabolism from butyric acid, and a substance which inhibits metabolism from butyric acid. Of these, butyric acid is particularly preferred as a marker for determining sensitivity to L-OHP.

Another member of the marker for determining sensitivity to an anti-cancer agent of the present invention is 4-methylpyrazole or a substance involved in 4-methylpyrazole metabolism (also called a 4-methylpyrazole-metabolism-related substance). The substance encompasses 4-methylpyrazole and all the substances that can vary the 4-methylpyrazole level in the metabolism thereof. Examples of such metabolism-related substances include a substance which promotes metabolism to 4-methylpyrazole, a substance which inhibits metabolism to 4-methylpyrazole, a substance which promotes metabolism from 4-methylpyrazole, and a substance which inhibits metabolism from 4-methylpyrazole. Of these, 4-methylpyrazole is particularly preferred as a marker for determining sensitivity to L-OHP and as a marker for determining sensitivity to 5-FU.

Another member of the marker for determining sensitivity to an anti-cancer agent of the present invention is isobutylamine or a substance involved in isobutylamine metabolism (also called an isobutylamine-metabolism-related substance). The substance encompasses isobutylamine and all the substances that can vary the isobutylamine level in the metabolism thereof. Examples of such metabolism-related substances include a substance which promotes metabolism to isobutylamine, a substance which inhibits metabolism to isobutylamine, a substance which promotes metabolism from isobutylamine, and a substance which inhibits metabolism from isobutylamine. Of these, isobutylamine is particularly preferred as a marker for determining sensitivity to 5-FU.

Another member of the marker for determining sensitivity to an anti-cancer agent of the present invention is glycolic acid or a substance involved in glycolic acid metabolism (also called a glycolic-acid-metabolism-related substance). The substance encompasses glycolic acid and all the substances that can vary the glycolic acid level in the metabolism thereof. Examples of such metabolism-related substances include a substance which promotes metabolism to glycolic acid, a substance which inhibits metabolism to glycolic acid, a substance which promotes metabolism from glycolic acid, and a substance which inhibits metabolism from glycolic acid. Of these, glycolic acid is particularly preferred as a marker for determining sensitivity to 5-FU.

Another member of the marker for determining sensitivity to an anti-cancer agent of the present invention is NADH or a substance involved in NADH metabolism (also called an NADH-metabolism-related substance). The substance encompasses NADH and all the substances that can vary the NADH level in the metabolism thereof. Examples of such metabolism-related substances include a substance which promotes metabolism to NADH, a substance which inhibits metabolism to NADH, a substance which promotes metabolism from NADH, and a substance which inhibits metabolism from NADH. Of these, NADH is particularly preferred as a marker for determining sensitivity to 5-FU.

Another member of the marker for determining sensitivity to an anti-cancer agent of the present invention is $NAD^+$ or a substance involved in $NAD^+$ metabolism (also called an $NAD^+$-metabolism-related substance). The substance encompasses $NAD^+$ and all the substances that can vary the $NAD^+$ level in the metabolism thereof. Examples of such metabolism-related substances include a substance which promotes metabolism to $NAD^+$, a substance which inhibits metabolism to $NAD^+$, a substance which promotes metabolism from $NAD^+$, and a substance which inhibits metabolism from $NAD^+$. Of these, $NAD^+$ is particularly preferred as a marker for determining sensitivity to 5-FU.

PRPP, $NAD^+$, NADH, and $NADP^+$ are known to be involved in various metabolic processes and to be nucleic-acid-metabolism-related substances.

Among the aforementioned markers for determining sensitivity to an anti-cancer agent, asparagine, spermine, spermidine, glutathione (GSH), γ-aminobutyric acid (GABA), 1-methyladenosine, γ-Glu-Cys, aspartic acid, and S-adenosylhomocysteine were previously confirmed, by the present inventors, to serve as markers that can determine sensitivity of a cancer patient to irinotecan, SN-38, or a salt thereof. The present inventors have newly found that asparagine, spermine, spermidine, glutathione (GSH), γ-Glu-Cys, and S-adenosylhomocysteine can serve as markers that can determine sensitivity of a cancer patient to anti-cancer agents including oxaliplatin (L-OHP) and/or a salt thereof. The inventors have also found that aspartic acid, spermidine, glutathione (GSH), GABA, 1-methyladenosine, and S-adenosylhomocysteine can serve as markers that can determine sensitivity of a cancer patient to anti-cancer agents including 5-FU. Notably, spermine and spermidine are involved in various types of metabolic pathways, and are known to be polyamine-metabolism-related substances.

As shown in the Examples described hereinbelow, β-alanine, Glu, Lys, $N^6$-acetyllysine, N-acetylornithine, γ-Glu-Cys, β-Ala-Lys, Glu-Glu, S-lactoylglutathione, cadaverine, cysteic acid, trans-cinnamic acid, S-adenosylhomocysteine, putrescine, $N^1$-acetylspermine, $N^8$-acetylspermidine, spermine, N-acetylputrescine, dTMP, CMP, UMP, GMP, CDP, UDP, dCTP, CTP, UTP, GTP, $NADP^+$, ATP and/or dGTP, guanosine, 2,3-diphosphoglyceric acid, pyruvic acid, malic acid, lauric acid, and 6-phosphogluconic acid exhibited a considerable intracellular level increase in HCT116 cells, which have high sensitivity to L-OHP, after exposure to L-OHP. In contrast, in DLD-1 cells, which have low sensitivity to L-OHP, these substances exhibited an intracellular level variation that was not so considerable, as compared with the case of HCT116 cells, or exhibited a drop in intracellular level as compared with a control group. Therefore, these substances are particularly useful as markers for determining sensitivity of a cancer patient to an anti-cancer agent such as L-OHP.

As shown in the Examples described hereinbelow, glutathione (GSH), butyric acid, and 4-methylpyrazole exhibited a considerable intracellular level increase in DLD-1 cells, which have low sensitivity to L-OHP, after exposure to L-OHP. In contrast, in HCT116 cells, which have high sensitivity to L-OHP, these substances exhibited an intracellular level variation that was not so considerable, as compared with the case of DLD-1 cells, or exhibited a drop in intracellular level as compared with a control group. Therefore, these substances are particularly useful as markers for determining sensitivity of a cancer patient to an anti-cancer agent such as L-OHP.

As shown in the Examples described hereinbelow, IMP exhibited a considerable intracellular level drop in HCT116 cells, which have high sensitivity to L-OHP, after exposure to L-OHP. In contrast, in DLD-1 cells, which have low sensitivity to L-OHP, IMP exhibited an intracellular level increase, as compared with a control group. Therefore, IMP is particularly useful as a marker for determining sensitivity of a cancer patient to an anti-cancer agent such as L-OHP.

As shown in the Examples described hereinbelow, N-acetylaspartic acid was investigated by use of 10 human cancer cell lines. As a result, N-acetylaspartic acid exhibited a high intracellular level in L-OHP-high-sensitive cells, and a low intracellular level in L-OHP-low-sensitive cells. Therefore, N-acetylaspartic acid is particularly useful as a marker for determining sensitivity of a cancer patient to an anti-cancer agent such as L-OHP.

As shown in the Examples described hereinbelow, N-acetylglucosamine, 3-phosphoglycerate, fructose-1,6-diphosphate, and ornithine were investigated by use of 10 human cancer cell lines. As a result, these substances exhibited a high intracellular level in L-OHP-low-sensitive cells, and a low intracellular level in L-OHP-high-sensitive cells. Therefore, N-acetylglucosamine, 3-phosphoglycerate, fructose-1,6-diphosphate, and ornithine are particularly useful as markers for determining sensitivity of a cancer patient to an anti-cancer agent such as L-OHP.

As shown in the Examples described hereinbelow, asparagine and N-acetyl-β-alanine were investigated by use of 10 human cancer cell lines. As a result, these substances exhibited a high intracellular level in L-OHP-high-sensitive cells, and a low intracellular level in L-OHP-low-sensitive cells. In addition, these substances exhibited a considerable intracellular level increase in HCT116 cells, which have high sensitivity to L-OHP, after exposure to L-OHP. In contrast, in DLD-1 cells, which have low sensitivity to L-OHP, these substances exhibited an intracellular level variation that was not so considerable, as compared with the case of HCT116 cells, which have high sensitivity to L-OHP. Therefore, asparagine and N-acetyl-β-alanine are particularly useful as markers for determining sensitivity of a cancer patient to an anti-cancer agent such as L-OHP.

As shown in the Examples described hereinbelow, arginine and spermidine were investigated by use of 10 human cancer cell lines. As a result, these substances exhibited a high intracellular level in L-OHP-low-sensitive cells, and a low intracellular level in L-OHP-high-sensitive cells. In addition, these substances exhibited a considerable intracellular level increase in HCT116 cells, which have high sensitivity to L-OHP, after exposure to L-OHP. In contrast, in DLD-1 cells, which have low sensitivity to L-OHP, these substances exhibited an intracellular level variation that was not so considerable, as compared with the case of HCT116 cells, which have high sensitivity to L-OHP, or exhibited a drop in intracellular level as compared with a control group. Therefore, arginine and spermidine are particularly useful as markers for determining sensitivity of a cancer patient to an anti-cancer agent such as L-OHP.

As shown in the Examples described hereinbelow, Asp, ornithine, N-acetylornithine, β-Ala-Lys, Glu-Glu, 2-aminoadipic acid, γ-aminobutyric acid, S-adenosylhomocysteine, guanosine, CMP, UMP, 1-methyladenosine, UDP, CTP, sedoheptulose 7-phosphate, dihydroxyacetone phosphate, pyruvic acid, malic acid, $N^1$-acetylspermine, isobutylamine, and glycolic acid exhibited a considerable intracellular level increase in HCT116 cells, which have high sensitivity to 5-FU, after exposure to 5-FU. In contrast, in DLD-1 cells, which have low sensitivity to 5-FU, these substances exhibited an intracellular level variation that was not so considerable, as compared with the case of HCT116 cells, or exhibited a drop in intracellular level as compared with a control group. Therefore, these substances are particularly useful as markers for determining sensitivity of a cancer patient to an anti-cancer agent such as 5-FU.

As shown in the Examples described hereinbelow, Ser, glutathione (GSH), and adenosine exhibited a considerable intracellular level increase in DLD-1 cells, which have low sensitivity to 5-FU, after exposure to 5-FU. In contrast, in HCT116 cells, which have high sensitivity to 5-FU, these substances exhibited an intracellular level variation that was not so considerable, as compared with the case of DLD-1 cells, or exhibited a drop in intracellular level as compared with a control group. Therefore, these substances are particularly useful as markers for determining sensitivity of a cancer patient to an anti-cancer agent such as 5-FU.

As shown in the Examples described hereinbelow, 3-methylhistidine, cadaverine, PRPP, and 4-methylpyrazole exhibited a considerable drop in intracellular level in HCT116 cells, which have high sensitivity to 5-FU, after exposure to 5-FU. In contrast, in DLD-1 cells, which have low sensitivity to 5-FU, these substances exhibited an intracellular level variation that was not so considerable, as compared with the case of HCT116 cells, or exhibited a rise in intracellular level as compared with a control group. Therefore, these substances are particularly useful as markers for determining sensitivity of a cancer patient to an anti-cancer agent such as 5-FU.

As shown in the Examples described hereinbelow, cysteine-glutathione, 2,3-diphosphoglyceric acid, N-acetylputrescine, $N^8$-acetylspermidine, putrescine, spermidine, 6-phosphogluconic acid, NADH, and $NAD^+$ exhibited a considerable drop in intracellular level in DLD-1 cells, which have low sensitivity to 5-FU, after exposure to 5-FU. In contrast, in HCT116 cells, which have high sensitivity to 5-FU, these substances exhibited an intracellular level variation that was not so considerable, as compared with the case of DLD-1 cells. Therefore, these substances are particularly useful as markers for determining sensitivity of a cancer patient to an anti-cancer agent such as 5-FU.

No particular limitation is imposed on the anti-cancer agent to which the marker for determining sensitivity to an anti-cancer agent of the present invention is applied. Examples of the anti-cancer agent include oxaliplatin (L-OHP), cyclophosphamide, ifosfamide, thiotepa, melphalan, busulfan, nimustine, ranimustine, dacarbazine, procarbazine, temozolomide, cisplatin, carboplatin, nedaplatin, methotrexate, pemetrexed, fluorouracil, tegaful/uracil, doxifluridine, tegaful/gimeracil/oteracil, capecitabine, cytarabine, enocitabine, gemcitabine, 6-mercaptopurine, fuludarabin, pentostatin, cladribine, hydroxyurea, doxorubicin, epirubicin, daunorubicin, idarubicine, pirarubicin, mitoxantrone, amurubicin, actinomycin D, bleomycine, pepleomycin, mytomycin C, aclarubicin, zinostatin, vincristine, vindesine, vinblastine, vinorelbine, paclitaxel, docetaxel, irinotecan, irinotecan active metabolite (SN-38), nogitecan (topotecan), etoposide, prednisolone, dexamethasone, tamoxifen, toremifene, medroxyprogesterone, anastrozole, exemestane, letrozole, rituximab, imatinib, gefitinib, gemtuzumab/ozogamicin, bortezomib, erlotinib, cetuximab, bevacizumab, sunitinib, sorafenib, dasatinib, panitumumab, asparaginase, tretinoin, arsenic trioxide, folinate, levofolinate, salts thereof, and active metabolites thereof. Of these, platinum-based complex anti-cancer agents and fluoro-pyrimidine anti-cancer agents are preferred, with oxaliplatin, fluorouracil, and a salt thereof being particularly preferred.

As described above, oxaliplatin, a salt thereof, fluorouracil, and a salt thereof are examples of the anti-cancer agent to which the marker for determining sensitivity to an anti-cancer agent of the present invention is applied. However, in addition to oxaliplatin and fluorouracil, an anti-cancer agent that are metabolized in the body, to thereby being transformed to oxaliplatin or fluorouracil may be the anti-cancer agent to which the marker for determining sensitivity to an anti-cancer agent of the present invention is applied. Specifically, tegaful and capecitabine are known to be metabolized in the body, to thereby form fluorouracil. Thus, instead of fluorouracil, tegaful or capecitabine may be used as the anti-cancer agent to which the marker for determining sensitivity to an anti-cancer agent of the present invention is applied.

In order to determine sensitivity of a subject to an anti-cancer agent by use of the marker for determining sensitivity to an anti-cancer agent of the present invention, the level of any of these metabolism-related substances in a specimen may be measured. Examples of the specimen include biological samples derived from subjects having cancer (i.e., cancer patients) such as blood, serum, plasma, urine, tumor tissue and cells, ascitic fluid, pleural fluid, cerebrospinal fluid, feces, and sputum. Of these, serum is particularly preferred.

Examples of the target cancer of the present invention include lip, oral, pharyngeal cancers such as pharyngeal cancer; gastrointestinal cancers such as esophageal cancer, gastric cancer, and colorectal cancer; respiratory and intrathoracic organ cancers such as lung cancer; bone cancer and articular cartilage cancer; skin melanoma, squamous cell cancer, and other skin cancers; mesothelial and soft tissue cancers such as mesothelioma; female genital cancers such as breast cancer, uterine cancer, and ovarian cancer; male genital cancers such as prostate cancer; urinary tract cancers such as bladder cancer; eye, brain, and central nervous system cancers such as brain tumor; thyroid and other endocrine cancers; lymphoid tissue, hematopoietic tissue, and related tissue cancers such as non-Hodgkin's lymphoma and lymphoid leukemia; and metastatic cancers from these cancers as primary lesions. The present invention is particularly preferably applied to non-small-cell lung cancer, small-cell lung cancer, cervical cancer, ovarian cancer, gastric cancer, colorectal cancer, squamous cell cancer, and malignant lymphoma.

The means for measuring these metabolism-related substances in a specimen may be appropriately selected in accordance with the substance to be measured. Examples of the means include mass spectrometers (e.g., CE-TOFMS and gas chromatography-mass spectrometry (GC-MS)), HPLC, immunological assay, and biological assay.

In the case where any of β-alanine, Glu, Lys, $N^6$-acetyllysine, N-acetylornithine, γ-Glu-Cys, β-Ala-Lys, Glu-Glu, S-lactoylglutathione, cadaverine, cysteic acid, trans-cinnamic acid, S-adenosylhomocysteine, putrescine, $N^1$-acetylspermine, $N^8$-acetylspermidine, spermine, N-acetylputrescine, dTMP, CMP, UMP, GMP, CDP, UDP, dCTP, CTP, UTP, GTP, $NADP^+$, ATP and/or dGTP, guanosine, 2,3-diphosphoglyceric acid, pyruvic acid, malic acid, lauric acid, and 6-phosphogluconic acid is used, and the target anti-cancer agent is L-OHP, the sensitivity of a cancer patient to the anti-cancer agent is determined as follows. The level of any of these metabolism-related substances in a biological sample derived from the cancer patient is measured before and after administration of the anti-cancer agent. When the metabolism-related substance level increases or exceeds a predetermined standard level, after administration of the anti-cancer agent, the cancer is determined to have sensitivity to the anti-cancer agent, whereas when the substance level is constant or below a predetermined standard level, after administration of the anti-cancer agent, the cancer is determined to have no sensitivity to the anti-cancer agent.

When the cancer has no sensitivity to an anti-cancer agent, no pharmaceutical effect can be expected from the anti-cancer agent. If such an ineffective anti-cancer agent is continuously administered to the patient, the cancer may progress, and adverse events may be aggravated. Thus, the marker for determining sensitivity to an anti-cancer agent of the present invention may be employed not only to determine therapeutic response to the anti-cancer agent, but also to greatly contribute to prevention of aggravation of adverse events, which would otherwise be caused by continuous administration of an ineffective anti-cancer agent.

In the case where any of glutathione (GSH), butyric acid, and 4-methylpyrazole is used, and the target anti-cancer agent is L-OHP, the sensitivity of a cancer patient to the anti-cancer agent is determined as follows. The level of any of these metabolism-related substances in a biological sample derived from the cancer patient is measured before and after administration of the anti-cancer agent. When the metabolism-related substance level increases or exceeds a predetermined standard level, after administration of the anti-cancer agent, the cancer is determined to have no sensitivity to the anti-cancer agent, whereas when the substance level is constant or below a predetermined standard level, after administration of the anti-cancer agent, the cancer is determined to have sensitivity to the anti-cancer agent.

When the cancer has no sensitivity to an anti-cancer agent, no pharmaceutical effect can be expected from the anti-cancer agent. If such an ineffective anti-cancer agent is continuously administered to the patient, the cancer may progress, and adverse events may be aggravated. Thus, the marker for determining sensitivity to an anti-cancer agent of the present invention may be employed not only to determine therapeutic response to the anti-cancer agent, but also to greatly contribute to prevention of aggravation of adverse events, which would otherwise be caused by continuous administration of an ineffective anti-cancer agent.

In the case where IMP is used, and the target anti-cancer agent is L-OHP, the sensitivity of a cancer patient to the anti-cancer agent is determined as follows. The level of any of these metabolism-related substances in a biological sample derived from the cancer patient is measured before and after administration of the anti-cancer agent. When the metabolism-related substance level decreases or is below a predetermined standard level, after administration of the anti-cancer agent, the cancer is determined to have sensitivity to the anti-cancer agent, whereas when the substance level is constant or exceeds a predetermined standard level, after administration of the anti-cancer agent, the cancer is determined to have no sensitivity to the anti-cancer agent.

When the cancer has no sensitivity to an anti-cancer agent, no pharmaceutical effect can be expected from the anti-cancer agent. If such an ineffective anti-cancer agent is continuously administered to the patient, the cancer may progress, and adverse events may be aggravated. Thus, the marker for determining sensitivity to an anti-cancer agent of the present invention may be employed not only to determine therapeutic response to the anti-cancer agent, but also to greatly contribute to prevention of aggravation of adverse events, which would otherwise be caused by continuous administration of an ineffective anti-cancer agent.

In the case where N-acetylaspartic acid is used, and the target anti-cancer agent is L-OHP, the sensitivity of a cancer patient to the anti-cancer agent is determined as follows. When the metabolism-related substance level is found to be lower than a predetermined standard level, before administration of the anti-cancer agent or in an early stage after administration, the cancer is determined to have no sensitivity to the anti-cancer agent.

When the cancer has no sensitivity to an anti-cancer agent, no pharmaceutical effect can be expected from the anti-cancer agent. If such an ineffective anti-cancer agent is continuously administered to the patient, the cancer may progress, and adverse events may be aggravated. Thus, the marker for determining sensitivity to an anti-cancer agent of the present invention may be employed not only to determine therapeutic response to the anti-cancer agent, but also to greatly contribute to prevention of aggravation of adverse events, which would otherwise be caused by continuous administration of an ineffective anti-cancer agent.

In the case where any of N-acetylglucosamine, 3-phosphoglycerate, fructose-1,6-diphosphate, and ornithine is used, and the target anti-cancer agent is L-OHP, the sensitivity of a cancer patient to the anti-cancer agent is determined as follows. When the metabolism-related substance level is found to be higher than a predetermined standard level, before administration of the anti-cancer agent or in an early stage after administration, the cancer is determined to have no sensitivity to the anti-cancer agent.

When the cancer has no sensitivity to an anti-cancer agent, no pharmaceutical effect can be expected from the anti-cancer agent. If such an ineffective anti-cancer agent is continuously administered to the patient, the cancer may progress, and adverse events may be aggravated. Thus, the marker for determining sensitivity to an anti-cancer agent of the present invention may be employed not only to determine therapeutic response to the anti-cancer agent, but also to greatly contribute to prevention of aggravation of adverse events, which would otherwise be caused by continuous administration of an ineffective anti-cancer agent.

In the case where any of asparagine and N-acetyl-β-alanine is used, and the target anti-cancer agent is L-OHP, the sensitivity of a cancer patient to the anti-cancer agent is determined as follows. The level of any of these metabolism-related substances in a biological sample derived from the cancer patient is measured before and after administration of the anti-cancer agent. When the metabolism-related substance level increases or exceeds a predetermined standard level, after administration of the anti-cancer agent, the cancer is determined to have sensitivity to the anti-cancer agent, whereas when the substance level is constant or below a predetermined standard level, after administration of the anti-cancer agent, the cancer is determined to have no sensitivity to the anti-cancer agent.

When the level of any of the metabolism-related substances is found to be lower than a predetermined standard level of the substance before or in an early stage after administration of the anti-cancer agent, the cancer can be determined to have no sensitivity to the anti-cancer agent. When the cancer has no sensitivity to an anti-cancer agent, no pharmaceutical effect can be expected from the anti-cancer agent. If such an ineffective anti-cancer agent is continuously administered to the patient, the cancer may progress, and adverse events may be aggravated. Thus, the marker for determining sensitivity to an anti-cancer agent of the present invention may be employed not only to determine therapeutic response to the anti-cancer agent, but also to greatly contribute to prevention of aggravation of adverse events, which would otherwise be caused by continuous administration of an ineffective anti-cancer agent.

In the case where any of arginine and spermidine is used, and the target anti-cancer agent is L-OHP, the sensitivity of a cancer patient to the anti-cancer agent is determined as follows. The level of any of these metabolism-related substances in a biological sample derived from the cancer patient is measured before and after administration of the anti-cancer agent. When the metabolism-related substance level increases or exceeds a predetermined standard level, after administration of the anti-cancer agent, the cancer is determined to have sensitivity to the anti-cancer agent, whereas when the substance level is constant or below a predetermined standard level, after administration of the anti-cancer agent, the cancer is determined to have no sensitivity to the anti-cancer agent.

When the level of any of the metabolism-related substances is found to be higher than a predetermined standard level of the substance before or in an early stage after administration of the anti-cancer agent, the cancer can be determined to have no sensitivity to the anti-cancer agent. When the cancer has no sensitivity to an anti-cancer agent, no pharmaceutical effect can be expected from the anti-cancer agent. If such an ineffective anti-cancer agent is continuously administered to the patient, the cancer may progress, and adverse events may be aggravated. Thus, the anti-cancer agent sensitivity determination marker of the present invention may be employed not only to determine therapeutic response to the anti-cancer agent, but also to greatly contribute to prevention of aggravation of adverse events, which would otherwise be caused by continuous administration of an ineffective anti-cancer agent.

In the case where any of Asp, ornithine, N-acetylornithine, β-Ala-Lys, Glu-Glu, 2-aminoadipic acid, γ-aminobutyric acid, S-adenosylhomocysteine, guanosine, CMP, UMP, 1-methyladenosine, UDP, CTP, sedoheptulose 7-phosphate, dihydroxyacetone phosphate, pyruvic acid, malic acid, $N^1$-acetylspermine, isobutylamine, and glycolic acid is used, and the target anti-cancer agent is 5-FU, the sensitivity of a cancer patient to the anti-cancer agent is determined as follows. The level of any of these metabolism-related substances in a biological sample derived from the cancer patient is measured before and after administration of the anti-cancer agent. When the metabolism-related substance level increases or exceeds a predetermined standard level, after administration of the anti-cancer agent, the cancer is determined to have sensitivity to the anti-cancer agent, whereas when the substance level is constant or below a predetermined standard level, after administration of the anti-cancer agent, the cancer is determined to have no sensitivity to the anti-cancer agent.

When the cancer has no sensitivity to an anti-cancer agent, no pharmaceutical effect can be expected from the anti-cancer agent. If such an ineffective anti-cancer agent is continuously administered to the patient, the cancer may progress, and adverse events may be aggravated. Thus, the marker for determining sensitivity to an anti-cancer agent of the present invention may be employed not only to determine therapeutic response to the anti-cancer agent, but also to greatly contribute to prevention of aggravation of adverse events, which would otherwise be caused by continuous administration of an ineffective anti-cancer agent.

In the case where any of Ser, glutathione (GSH), and adenosine is used, and the target anti-cancer agent is 5-FU, the sensitivity of a cancer patient to the anti-cancer agent is determined as follows. The level of any of these metabolism-related substances in a biological sample derived from the cancer patient is measured before and after administration of the anti-cancer agent. When the metabolism-related substance level increases or exceeds a predetermined standard level, after administration of the anti-cancer agent, the cancer is determined to have no sensitivity to the anti-cancer agent, whereas when the substance level is constant or below a predetermined standard level, after administration of the anti-cancer agent, the cancer is determined to have sensitivity to the anti-cancer agent.

When the cancer has no sensitivity to an anti-cancer agent, no pharmaceutical effect can be expected from the anti-cancer agent. If such an ineffective anti-cancer agent is continuously administered to the patient, the cancer may progress, and adverse events may be aggravated. Thus, the marker for determining sensitivity to an anti-cancer agent of the present invention may be employed not only to determine therapeutic response to the anti-cancer agent, but also to greatly contribute to prevention of aggravation of adverse events, which would otherwise be caused by continuous administration of an ineffective anti-cancer agent.

In the case where any of 3-methylhistidine, cadaverine, PRPP, and 4-methylpyrazole is used, and the target anti-cancer agent is 5-FU, the sensitivity of a cancer patient to the anti-cancer agent is determined as follows. The level of any of these metabolism-related substances in a biological sample derived from the cancer patient is measured before and after administration of the anti-cancer agent. When the metabolism-related substance level decreases or is below a predetermined standard level, after administration of the anti-cancer agent, the cancer is determined to have sensitivity to the anti-cancer agent, whereas when the substance level is constant or exceeds a predetermined standard level, after administration of the anti-cancer agent, the cancer is determined to have no sensitivity to the anti-cancer agent.

When the cancer has no sensitivity to an anti-cancer agent, no pharmaceutical effect can be expected from the anti-cancer agent. If such an ineffective anti-cancer agent is continuously administered to the patient, the cancer may progress, and adverse events may be aggravated. Thus, the marker for determining sensitivity to an anti-cancer agent of the present invention may be employed not only to determine therapeutic response to the anti-cancer agent, but also to greatly contribute to prevention of aggravation of adverse events, which would otherwise be caused by continuous administration of an ineffective anti-cancer agent.

In the case where any of cysteine-glutathione, 2,3-diphosphoglyceric acid, N-acetylputrescine, $N^8$-acetylspermidine, putrescine, spermidine, 6-phosphogluconic acid, NADH, and $NAD^+$ is used, and the target anti-cancer agent is 5-FU, the sensitivity of a cancer patient to the anti-cancer agent is determined as follows. The level of any of these metabolism-related substances in a biological sample derived from the cancer patient is measured before and after administration of the anti-cancer agent. When the metabolism-related substance level decreases or is below a predetermined standard level, after administration of the anti-cancer agent, the cancer is determined to have no sensitivity to the anti-cancer agent, whereas when the substance level is constant or exceeds a predetermined standard level, after administration of the anti-cancer agent, the cancer is determined to have sensitivity to the anti-cancer agent.

When the cancer has no sensitivity to an anti-cancer agent, no pharmaceutical effect can be expected from the anti-cancer agent. If such an ineffective anti-cancer agent is continuously administered to the patient, the cancer may progress, and adverse events may be aggravated. Thus, the marker for determining sensitivity to an anti-cancer agent of the present invention may be employed not only to determine therapeutic response to the anti-cancer agent, but also to greatly contribute to prevention of aggravation of adverse events, which would otherwise be caused by continuous administration of an ineffective anti-cancer agent.

In order to carry out the method of the present invention for determining sensitivity of a specimen to an anti-cancer agent, preferably, a kit containing a protocol for measuring any of the metabolism-related substances in a specimen is employed. The kit contains a reagent for measuring any of these metabolism-related substances, an indication of an instruction manual for use of the reagent, standards for determining the presence or absence of sensitivity to the anti-cancer agent, etc. The standards include (relative) standard levels of these metabolism-related substances, a (relative) high threshold level, a (relative) low threshold level, factors affecting the measurements, the degree of the effects, etc. These substance levels may be set so as to suit the target anti-cancer agent selected. The sensitivity determination may be performed as described above on the basis of the standards.

In the case where any of β-alanine, Glu, Lys, $N^6$-acetyllysine, N-acetylornithine, γ-Glu-Cys, β-Ala-Lys, Glu-Glu, S-lactoylglutathione, cadaverine, cysteic acid, trans-cinnamic acid, S-adenosylhomocysteine, putrescine, $N^1$-acetylspermine, $N^8$-acetylspermidine, spermine, N-acetylputrescine, dTMP, CMP, UMP, GMP, CDP, UDP, dCTP, CTP, UTP, GTP, $NADP^+$, ATP and/or dGTP, guanosine, 2,3-diphosphoglyceric acid, pyruvic acid, malic acid, lauric acid, and 6-phosphogluconic acid is used, and the target anti-cancer agent is L-OHP, screening of an anti-cancer agent sensitivity enhancer can be performed through employment, as an index, of variation in level of any of the substances after exposure to the anti-cancer agent, specifically, promotion of the variation or increase in level. That is, a substance which promotes variation in level of the metabolism-related substance(s) or which increases the metabolism-related substance level, in vitro or in vivo after exposure to the anti-cancer agent, enhances the sensitivity to the anti-cancer agent. For example, in an in vitro case, a substance which promotes variation in level of the metabolism-related substance(s) in cells or which increases the metabolism-related substance level after exposure to an anti-cancer agent can serve as a substance which enhances the sensitivity to the anti-cancer agent (i.e., anti-cancer agent sensitivity enhancer). Also, in an in vivo case, a substance which promotes variation in level of the metabolism-related substance(s) in a cancer-bearing animal or a substance which increases the metabolism-related substance level, after exposure to an anti-cancer agent, can serve as a substance which enhances the sensitivity to the anti-cancer agent (i.e., anti-cancer agent sensitivity enhancer).

In the case where any of glutathione (GSH), butyric acid, and 4-methylpyrazole is used, and the target anti-cancer agent is L-OHP, screening of an anti-cancer agent sensitivity enhancer can be performed through employment, as an index, of variation in level of any of the substances after exposure to the anti-cancer agent. That is, a substance which suppresses variation in level of glutathione (GSH), butyric acid, or 4-methylpyrazole, in vitro or in vivo after exposure to the anti-cancer agent, enhances the sensitivity to the anti-cancer agent. For example, in an in vitro case, a substance which suppresses variation in level of glutathione (GSH), butyric acid, or 4-methylpyrazole in cells after exposure to an anti-cancer agent can serve as a substance which enhances the sensitivity to the anti-cancer agent (i.e., anti-cancer agent sensitivity enhancer). Also, in an in vivo case, a substance which suppresses variation in level of glutathione (GSH), butyric acid, or 4-methylpyrazole in a cancer-bearing animal, after exposure to an anti-cancer agent, can serve as a substance which enhances the sensitivity to the anti-cancer agent (i.e., anti-cancer agent sensitivity enhancer).

In the case where IMP is used, and the target anti-cancer agent is L-OHP, screening of an anti-cancer agent sensitivity enhancer can be performed through employment, as an index, of variation in level of IMP after exposure to the anti-cancer agent, specifically, promotion of the variation or decrease in IMP level. That is, a substance which promotes the variation or which decreases the IMP level, in vitro or in vivo after exposure to the anti-cancer agent, enhances the sensitivity to the anti-cancer agent. For example, in an in vitro case, a substance which promotes the variation or which decreases the IMP level in cells after exposure to an anti-cancer agent can serve as a substance which enhances the sensitivity to the anti-cancer agent (i.e., anti-cancer agent sensitivity enhancer). Also, in an in vivo case, a substance which promotes the variation in a cancer-bearing animal or a substance which decreases the IMP level, after exposure to an anti-cancer agent, can serve as a substance which enhances the sensitivity to the anti-cancer agent (i.e., anti-cancer agent sensitivity enhancer).

In the case where N-acetylaspartic acid is used, and the target anti-cancer agent is L-OHP, screening of an anti-cancer agent sensitivity enhancer can be performed through employment, as an index, of variation in level of N-acetylaspartic acid after exposure to the anti-cancer agent, specifically, increase in N-acetylaspartic acid level. That is, a substance which increases the N-acetylaspartic acid level, in vitro or in vivo before exposure to the anti-cancer agent, enhances the sensitivity to the anti-cancer agent. For example, in an in vitro case, a substance which increases the N-acetylaspartic acid level in various cancer cells which have been treated with the substance before exposure to an anti-cancer agent can serve as a substance which enhances the sensitivity to the anti-cancer agent (i.e., anti-cancer agent sensitivity enhancer). Also, in an in vivo case, a substance which increases the N-acetylaspartic acid level in a cancer-bearing animal before exposure to an anti-cancer agent, can serve as a substance which enhances the sensitivity to the anti-cancer agent (i.e., anti-cancer agent sensitivity enhancer).

In the case where any of N-acetylglucosamine, 3-phosphoglycerate, fructose-1,6-diphosphate, and ornithine is used, and the target anti-cancer agent is L-OHP, screening of an anti-cancer agent sensitivity enhancer can be performed through employment, as an index, of variation in level of the substance(s) after exposure to the anti-cancer agent, specifically, decrease in N-acetylglucosamine level, 3-phosphoglycerate level, fructose-1,6-diphosphate level, or ornithine level. That is, a substance which decreases such a level, in vitro or in vivo before exposure to the anti-cancer agent, enhances the sensitivity to the anti-cancer agent. For example, in an in vitro case, a substance which decreases the level in various cancer cells which have been treated with the substance before exposure to an anti-cancer agent can serve as a substance which enhances the sensitivity to the anti-cancer agent (i.e., anti-cancer agent sensitivity enhancer). Also, in an in vivo case, a substance which decreases the level in a cancer-bearing animal before exposure to an anti-cancer agent, can serve as a substance which enhances the sensitivity to the anti-cancer agent (i.e., anti-cancer agent sensitivity enhancer).

In the case where any of asparagine and N-acetyl-β-alanine is used, and the target anti-cancer agent is L-OHP, screening of an anti-cancer agent sensitivity enhancer can be performed through employment, as an index, of variation in level of asparagine or N-acetyl-β-alanine after exposure to the anti-cancer agent, specifically, promotion of the variation or increase in asparagine level or N-acetyl-β-alanine level. That is, a substance which increases such a level in vitro or in vivo before exposure to the anti-cancer agent, or a substance which promotes variation in level or which increases the level in vitro or in vivo after exposure to the anti-cancer agent, enhances the sensitivity to the anti-cancer agent. For example, in an in vitro case, a substance which increases the level in various cancer cells which have been treated with the substance before exposure to an anti-cancer agent can serve as a substance which enhances the sensitivity to the anti-cancer agent (i.e., anti-cancer agent sensitivity enhancer). Also, in an in vitro case, a substance which promotes the variation or increases the level in various cancer cells which have been treated with the substance after exposure to an anti-cancer agent can serve as a substance which enhances the sensitivity to the anti-cancer agent (i.e., anti-cancer agent sensitivity enhancer). In an in vivo case, a substance which increases the asparagine level or N-acetyl-β-alanine level in a cancer-bearing animal before exposure to an anti-cancer agent, or a substance which increases the asparagine level or N-acetyl-β-alanine level or which promotes the variation after exposure to the anti-cancer agent, can serve as a substance which enhances the sensitivity to the anti-cancer agent (i.e., anti-cancer agent sensitivity enhancer).

In the case where any of arginine and spermidine is used, and the target anti-cancer agent is L-OHP, screening of an anti-cancer agent sensitivity enhancer can be performed through employment, as an index, of variation in level of arginine or spermidine after exposure to the anti-cancer agent. That is, a substance which decreases arginine level or spermidine level in vitro or in vivo before exposure to the anti-cancer agent, or a substance which promotes the variation or which increases the level in vitro or in vivo after exposure to the anti-cancer agent, enhances the sensitivity to the anti-cancer agent. For example, in an in vitro case, a substance which decreases the level in various cancer cells which have been treated with the substance before exposure to an anti-cancer agent can serve as a substance which enhances the sensitivity to the anti-cancer agent (i.e., anti-cancer agent sensitivity enhancer). In another in vitro case, a substance which promotes variation in level of arginine or spermidine or which increases the level in various cancer cells after exposure to an anti-cancer agent can serve as a substance which enhances the sensitivity to the anti-cancer agent (i.e., anti-cancer agent sensitivity enhancer). Also, in an in vivo case, a substance which decreases the arginine level or spermidine level in a cancer-bearing animal before exposure to an anti-cancer agent, or a substance which promotes variation in level of arginine or spermidine or which increases the level thereof after exposure to the anti-cancer agent, can serve as a substance which enhances the sensitivity to the anti-cancer agent (i.e., anti-cancer agent sensitivity enhancer).

In the case where any of Asp, ornithine, N-acetylornithine, β-Ala-Lys, Glu-Glu, 2-aminoadipic acid, γ-aminobutyric acid, S-adenosylhomocysteine, guanosine, CMP, UMP, 1-methyladenosine, UDP, CTP, sedoheptulose 7-phosphate, dihydroxyacetone phosphate, pyruvic acid, malic acid, $N^1$-acetylspermine, isobutylamine, and glycolic acid is used, and the target anti-cancer agent is 5-FU, screening of an anti-cancer agent sensitivity enhancer can be performed through employment, as an index, of variation in level of any of the substances, specifically, promotion of the variation or increase in level. That is, a substance which promotes variation in level of the metabolism-related substance(s) or which increases the metabolism-related substance level, in vitro or in vivo after exposure to the anti-cancer agent, enhances the sensitivity to the anti-cancer agent. For example, in an in vitro case, a substance which promotes variation in level of the metabolism-related substance(s) in cells or increases the level after exposure to an anti-cancer agent can serve as a substance which enhances the sensitivity to the anti-cancer agent (i.e., anti-cancer agent sensitivity enhancer). Also, in an in vivo case, a substance which promotes variation in level of the metabolism-related substance(s) in a cancer-bearing animal or a substance which increases the level, after exposure to an anti-cancer agent, can serve as a substance which enhances the sensitivity to the anti-cancer agent (i.e., anti-cancer agent sensitivity enhancer).

In the case where any of Ser, glutathione (GSH), and adenosine is used, and the target anti-cancer agent is 5-FU, screening of an anti-cancer agent sensitivity enhancer can be performed through employment, as an index, of variation in level of any of the substances after exposure to the anti-cancer agent. That is, a substance which suppresses variation in level of Ser, glutathione (GSH), or adenosine, in vitro or in vivo after exposure to the anti-cancer agent, enhances the sensitivity to the anti-cancer agent. For example, in an in vitro case, a substance which suppresses variation in level of Ser, glutathione (GSH), or adenosine in cells after exposure to an anti-cancer agent can serve as a substance which enhances the sensitivity to the anti-cancer agent (i.e., anti-cancer agent sensitivity enhancer). Also, in an in vivo case, a substance which suppresses variation in level of Ser, glutathione (GSH), or adenosine in a cancer-bearing animal, after exposure to an anti-cancer agent, can serve as a substance which enhances the sensitivity to the anti-cancer agent (i.e., anti-cancer agent sensitivity enhancer).

In the case where any of 3-methylhistidine, cadaverine, PRPP, and 4-methylpyrazole is used, and the target anti-cancer agent is 5-FU, screening of an anti-cancer agent sensitivity enhancer can be performed through employment, as an index, of variation in level of any of these substances after exposure to the anti-cancer agent, specifically, promotion of the variation or decrease in the 3-methylhistidine level, cadaverine level, PRPP level, or 4-methylpyrazole level. That is, a substance which promotes the variation or which decreases the level, in vitro or in vivo after exposure to the anti-cancer agent, enhances the sensitivity to the anti-cancer agent. For example, in an in vitro case, a substance which promotes the variation or which decreases the 3-methylhistidine level, cadaverine level, PRPP level, or 4-methylpyrazole level in cells after exposure to an anti-cancer agent can serve as a substance which enhances the sensitivity to the anti-cancer agent (i.e., anti-cancer agent sensitivity enhancer). Also, in an in vivo case, a substance which promotes the variation in a cancer-bearing animal or a substance which decreases the 3-methylhistidine level, cadaverine level, PRPP level, or 4-methylpyrazole level, after exposure to an anti-cancer agent, can serve as a substance which enhances the sensitivity to the anti-cancer agent (i.e., anti-cancer agent sensitivity enhancer).

In the case where any of cysteine-glutathione, 2,3-diphosphoglyceric acid, N-acetylputrescine, $N^8$-acetylspermidine, putrescine, spermidine, 6-phosphogluconic acid, NADH, and $NAD^+$ is used, and the target anti-cancer agent is 5-FU, screening of an anti-cancer agent sensitivity enhancer can be performed through employment, as an index, of variation in level of any of the substances after exposure to the anti-cancer agent. That is, a substance which suppresses variation in level of any of the substances, in vitro or in vivo after exposure to the anti-cancer agent, enhances the sensitivity to the anti-cancer agent. For example, in an in vitro case, a substance which suppresses variation in level of any of the metabolism-related substances in cells after exposure to an anti-cancer agent can serve as a substance which enhances the sensitivity to the anti-cancer agent (i.e., anti-cancer agent sensitivity enhancer). Also, in an in vivo case, a substance which suppresses variation in level of any of the metabolism-related substances in a cancer-bearing animal, after exposure to an anti-cancer agent, can serve as a substance which enhances the sensitivity to the anti-cancer agent (i.e., anti-cancer agent sensitivity enhancer).

Screening of an anti-cancer agent can be performed by means of the marker for determining sensitivity to an anti-cancer agent of the present invention as an index. That is, a substance which can vary the level of the marker for determining sensitivity to an anti-cancer agent in vitro or in vivo is evaluated as an anti-cancer agent. For example, in an in vitro case, a substance which varies the level of the marker for determining sensitivity to an anti-cancer agent in various cancer cells after exposure to the substance can serve as an anti-cancer agent. Also, when the level of the marker for determining sensitivity to an anti-cancer agent in a cancer-bearing animal is varied after administration of a substance thereto, the substance can serve as an anti-cancer agent. If the anti-cancer agent is expected to exhibit a pharmaceutical effect, the variation in the level of the marker for determining sensitivity to an anti-cancer agent is observed before occurrence of tumor shrinkage or attaining cytocidal effect. Therefore, screening employing the level of the marker for determining sensitivity to an anti-cancer agent as an index can realize, for a shorter period of time, determination whether or not the test substance serves as a useful anti-cancer agent, whereby efforts and cost involved in the development of anti-cancer agents are greatly expected to be reduced.

Through employment, in combination, of the thus-obtained anti-cancer agent sensitivity enhancer and an anti-cancer agent which is a sensitivity enhancement target of the enhancer, the therapeutic effect of the anti-cancer agent is drastically enhanced. The combination of the anti-cancer agent sensitivity enhancer and the anti-cancer agent which is a sensitivity enhancement target of the enhancer may be a composition containing both ingredients, or a combined drug of preparations containing individual ingredients. These two ingredients may be administered through different routes. The target anti-cancer agents which may be employed here are the same as described above. Examples of the anti-cancer agent include oxaliplatin, cyclophosphamide, ifosfamide, thiotepa, melphalan, busulfan, nimustine, ranimustine, dacarbazine, procarbazine, temozolomide, cisplatin, carboplatin, nedaplatin, methotrexate, pemetrexed, fluorouracil, tegaful/uracil, doxifluridine, tegaful/gimeracil/oteracil, capecitabine, cytarabine, enocitabine, gemcitabine, 6-mercaptopurine, fuludarabin, pentostatin, cladribine, hydroxyurea, doxorubicin, epirubicin, daunorubicin, idarubicine, pirarubicin, mitoxantrone, amurubicin, actinomycin D, bleomycine, pepleomycin, mytomycin C, aclarubicin, zinostatin, vincristine, vindesine, vinblastine, vinorelbine, paclitaxel, docetaxel, irinotecan, irinotecan-active metabolite (SN-38), nogitecan (topotecan), etoposide, prednisolone, dexamethasone, tamoxifen, toremifene, medroxyprogesterone, anastrozole, exemestane, letrozole, rituximab, imatinib, gefitinib, gemtuzumab/ozogamicin, bortezomib, erlotinib, cetuximab, bevacizumab, sunitinib, sorafenib, dasatinib, panitumumab, asparaginase, tretinoin, arsenic trioxide, folinate, levofolinate, salts thereof, and active metabolites thereof. Of these, platinum-based complex anti-cancer agents and fluoro-pyrimidine anti-cancer agents are preferred, with oxaliplatin, fluorouracil, and a salt thereof being particularly preferred.

EXAMPLES

The present invention will next be described in more detail by way of examples.

Example 1

(1) Method
(a) Cells Employed

Ten human colorectal cancer cell lines (DLD-1, HCT15, HCT116, HT29, Lovo, LS174T, SW480, SW620, SW1116, and WiDr) were employed. HCT116 and HT29 were obtained from Kabushiki Kaisha Yakult Honsha. DLD-1, Lovo, SW480, SW1116, and WiDr were obtained from Dainippon Sumitomo Pharma Co., Ltd. HCT15 and LS174T were obtained from Cell Resource Center for Biomedical Research, Institute of Development, Aging and Cancer, Tohoku University. SW620 was obtained from Summit Pharmaceuticals International Corporation.

(b) Drug

L-OHP powder was obtained from Kabushiki Kaisha Yakult Honsha.

c) Evaluation of Sensitivity of Cancer to L-OHP

Cancer cells of each cell line were exposed to 0- to 1,000-μmol/L L-OHP for 48 hours and after drug exposure, cell viability was determined by means of an MTS assay (CellTiter96™AQ$_{ueous}$ One Solution Cell Proliferation Assay, Promega). $IC_{50}$ value (L-OHP concentration at which cell growth is inhibited by 50% as compared with L-OHP-non-treated sample) was calculated, and sensitivity of each cell line to L-OHP was evaluated by the $IC_{50}$ value as an index.

(d) Recovery of Metabolites in the Cells

From cultured cells of each cell line in a steady state, the culture medium was removed. Then, the cells were washed on ice with 5% mannitol (4° C.). Immediately thereafter, methanol (4° C., containing an internal standard) was added to the washed cells, to thereby inactivate present enzymes, and the cells were stored at −80° C. Separately, cells for cell count were provided in addition to the cells from which metabolites were extracted, and then subjected to the same treatment before performing cell count. The data were employed in correction of the cell counts.

(e) Preparation of Metabolomic Sample

Chloroform and Milli-Q water were added to the methanol solution stored at −80° C., and liquid-liquid extraction was performed, to thereby remove miscellaneous matters. A water-methanol layer containing metabolites was recovered and filtered through a centrifugal ultrafiltration membrane (fraction molecular weight: 5,000 Da), to thereby remove protein. The filtrate was dried under reduced pressure and then stored at −80° C. The filtrate was dissolved in Milli-Q water, and immediately after, the solution was subjected to metabolomic analysis.

(f) Metabolomic Analysis

Comprehensive analysis of intracellular metabolites was performed by means of a capillary electrophoresis-time-of-flight-type mass spectrometer (CE-TOFMS) (product of Agilent Technologies). In a cation mode or an anion mode, metabolites detected at m/z values of 50 to 1,000 were simultaneously quantitated.

(g) Relationship Between Intracellular Metabolite Level and Sensitivity to L-OHP Peaks attributed to metabolites present in each cell sample and detected through CE-TOFMS were analyzed with reference to about 500 reference samples having known m/z values and flight times. The thus-identified metabolites were investigated in terms of intracellular levels in ten human colorectal cancer cell lines, and the relationship between the metabolite level and the sensitivity of each cell line to L-OHP was studied.

(2) Results (a) Sensitivity of 10 Human Colorectal Cancer Cell Lines to L-OHP

The sensitivity of 10 human colorectal cancer cell lines (DLD-1, HCT15, HCT116, HT29, Lovo, LS174T, SW480, SW620, SW1116, and WiDr) to L-OHP was evaluated by $IC_{50}$ values calculated through the MTS assay as indices. Among them, SW480 (0.65±0.07 µM), Lovo (0.72±0.12 µM), and HCT116 (0.89±0.33 µM) exhibited high sensitivity, and SW1116 (26.42±4.12 µM), HT29 (23.92±9.29 µM), WiDr (17.30±5.24 µM), and DLD-1 (16.95±6.31 µM) exhibited low sensitivity (FIG. 1).

(b) Relationship Between Intracellular Metabolite Level and Sensitivity to L-OHP Intracellular metabolites were extracted from human colorectal cancer cells of 10 cell lines and simultaneously analyzed through CE-TOFMS. Some thousand peaks detected from the samples were analyzed with reference to about 500 reference samples. As a result, metabolites which were detected in any of the cell lines and identified were investigated. On the basis of the MTS assay, 10 human colorectal cancer cell lines were divided into five L-OHP-high-sensitive cell lines (HCT15, HCT116, Lovo, SW480, and SW620) and five L-OHP-low-sensitive cell lines (DLD-1, HT29, LS174T, SW1116, and WiDr), and difference in intracellular metabolite level between the two groups was investigated. As a result, the metabolites exhibiting considerable difference in intracellular level between the L-OHP-high-sensitive group and the L-OHP-low-sensitive group were as follows: N-acetylglucosamine (p=0.0108), arginine (p=0.0263), asparagine (p=0.0794), 3-phosphoglycerate (p=0.0201), N-acetyl-β-alanine (p=0.0392), N-acetylaspartic acid (p=0.0529), and fructose-1,6-diphodphate (p=0.1071) (FIG. 2).

Example 2

(1) Method (a) Cells Employed

Among the cell lines employed in Example 1, two human colorectal cancer cell lines (HCT116 and DLD-1) were employed. Cell culturing was performed by means of a ϕ100 mm/Tissue Culture Dish (IWAKI) with a medium (Dulbecco's modified Eagle's Medium (DMEM) containing 10% fetal bovine serum (product of Invitrogen) at 37° C. under 5% $CO_2$ conditions.

(b) Drugs

L-OHP powder was obtained from Kabushiki Kaisha Yakult Honsha. 5-FU powder was obtained from Sigma Aldrich Japan K.K.

(c) Exposure to L-OHP and Recovery of Metabolites in the Cells

The two colorectal cancer cells were exposed to L-OHP by changing the culture medium to a medium containing L-OHP at 10 µmol/L. The same culture was performed in an L-OHP-free medium (control group). After exposure to L-OHP (0 hr, 4 hr, 12 hr, 24 hr, and 48 hr), the cells were washed on ice with 5%, mannitol (4° C.). Immediately thereafter, methanol (4° C., containing an internal standard) was added to the washed cells, to thereby inactivate present enzymes, and the cells were stored at −80° C. Separately, cells for cell count were provided in addition to the cells from which metabolites were extracted, and then subjected to the same treatment before performing cell count. The data were employed in correction of the cell counts.

(d) Exposure to 5-FU and Recovery of Metabolites in the Cells

The two colorectal cancer cells were exposed to 5-FU by changing the culture medium to a medium containing 5-FU at 100 µmol/L. The same culture was performed in a 5-FU-free medium (control group). After exposure to 5-FU (0 hr, 4 hr, 12 hr, 24 hr, and 48 hr), the cells were washed on ice with 5% mannitol (4° C.). Immediately thereafter, methanol (4° C., containing an internal standard) was added to the washed cells, to thereby inactivate present enzymes, and the cells were stored at −80° C. Separately, cells for cell count were provided in addition to the cells from which metabolites were extracted, and then subjected to the same treatment before performing cell count. The data were employed in correction of the cell counts.

(e) Preparation of Metabolomic Sample

Chloroform and Milli-Q water were added to the methanol solution stored at −80° C., and liquid-liquid extraction was performed, to thereby remove miscellaneous matters. A water-methanol layer containing metabolites was recovered and filtered through a centrifugal ultrafiltration membrane (fraction molecular weight: 5,000 Da), to thereby remove protein. The filtrate was dried under reduced pressure and then stored at −80° C. The filtrate was dissolved in Milli-Q water, and immediately after, the solution was subjected to metabolomic analysis.

(f) Metabolomic Analysis

Comprehensive analysis of intracellular metabolites was performed by means of a capillary electrophoresis-time-of-flight-type mass spectrometer (CE-TOFMS) (product of Agilent Technologies). In the comprehensive analysis of cationic metabolites, voltage was applied so that the outlet of the capillary served as a negative electrode, whereas in the comprehensive analysis of anionic metabolites, voltage was applied so that the outlet of the capillary served as a positive electrode. Metabolites detected at m/z values of 50 to 1,000 were simultaneously quantitated.

(2) Results

Human colorectal cancer cells of two cell lines having different sensitivities to L-OHP (high-sensitivity: HCT116, low-sensitivity: DLD-1) were exposed to 10 μM L-OHP for 0, 4, 12, 24, and 48 hours, and metabolites present in the cells were extracted. Each sample was analyzed through CE-TOFMS, to thereby simultaneously identify cationic, anionic, and nucleotide-related metabolites. About 170 metabolites, which had been detected and identified, were selected, and the time-dependent change in intracellular level of each metabolite after exposure to L-OHP was investigated. As a result, some metabolites were found to exhibit no considerable change in intracellular level in L-OHP-low-sensitivity cells (DLD-1) after exposure to L-OHP and a considerable increase in intracellular level in L-OHP-high-sensitivity cells (HCT116) after exposure to L-OHP. The metabolites were putrescine, $N^1$-acetylspermine, $N^8$-acetylspermidine, spermine, asparagine, and β-alanine (FIGS. 3 to 8).

Among the metabolites which exhibited a considerable difference in time-dependent change in intracellular level after exposure to L-OHP between the two cell lines, β-alanine exhibited a remarkable rise in intracellular level in HCT116 cells after 24-hour exposure to L-OHP. Since β-alanine is known to be a decomposition product in nucleic acid metabolism, variation in nucleic acid metabolism and variation in level of metabolites in close relation to nucleic acid metabolism after 24-hour exposure to L-OHP were investigated in L-OHP-high-sensitivity cells (HCT116) and L-OHP-low-sensitivity cells (DLD-1). As a result, in L-OHP-high-sensitivity cells, intracellular levels of many metabolites involved in the nucleic acid metabolism pathway were found to be elevated (FIG. 9). Particularly, considerable intracellular level rise was found in the cases of dTMP, CMP, UMP, GMP, CDP, UDP, dCTP, CTP, UTP, GTP, $NADP^+$, ATP and/or dGTP in HCT116 cells. In DLD-1 cells, variation in intracellular level was less considerable than that observed in HCT116 cells, or a drop in intracellular level with respect to a control group was observed. The ratio of intracellular level of each of the metabolites after 24-hour exposure to L-OHP to that of the control group was calculated in the cases of HCT116 and DLD-1. The ratio (HCT116/DLD-1) was 1.2 or higher in all cases.

A remarkable rise in intracellular level of IMP after exposure to L-OHP was observed in DLD-1 cells. However, in HCT116 cells, a drop in intracellular level of IMP was observed. The ratio of IMP intracellular level after 24-hour exposure to L-OHP to that of the control group was calculated in the cases of HCT116 and DLD-1. The ratio (HCT116/DLD-1) was as considerably low as 0.26.

The metabolites involved in the nucleic acid metabolism pathway were screened on the basis of a condition where the ratio is lower than 0.8 or 1.2 or higher. As a result, dTMP, CMP, UMP, IMP, GMP, CDP, UDP, dCTP, CTP, UTP, GTP, $NADP^+$, ATP and/or dGTP were selected to serve as markers for determining sensitivity to an anti-cancer agent.

Figure 10:
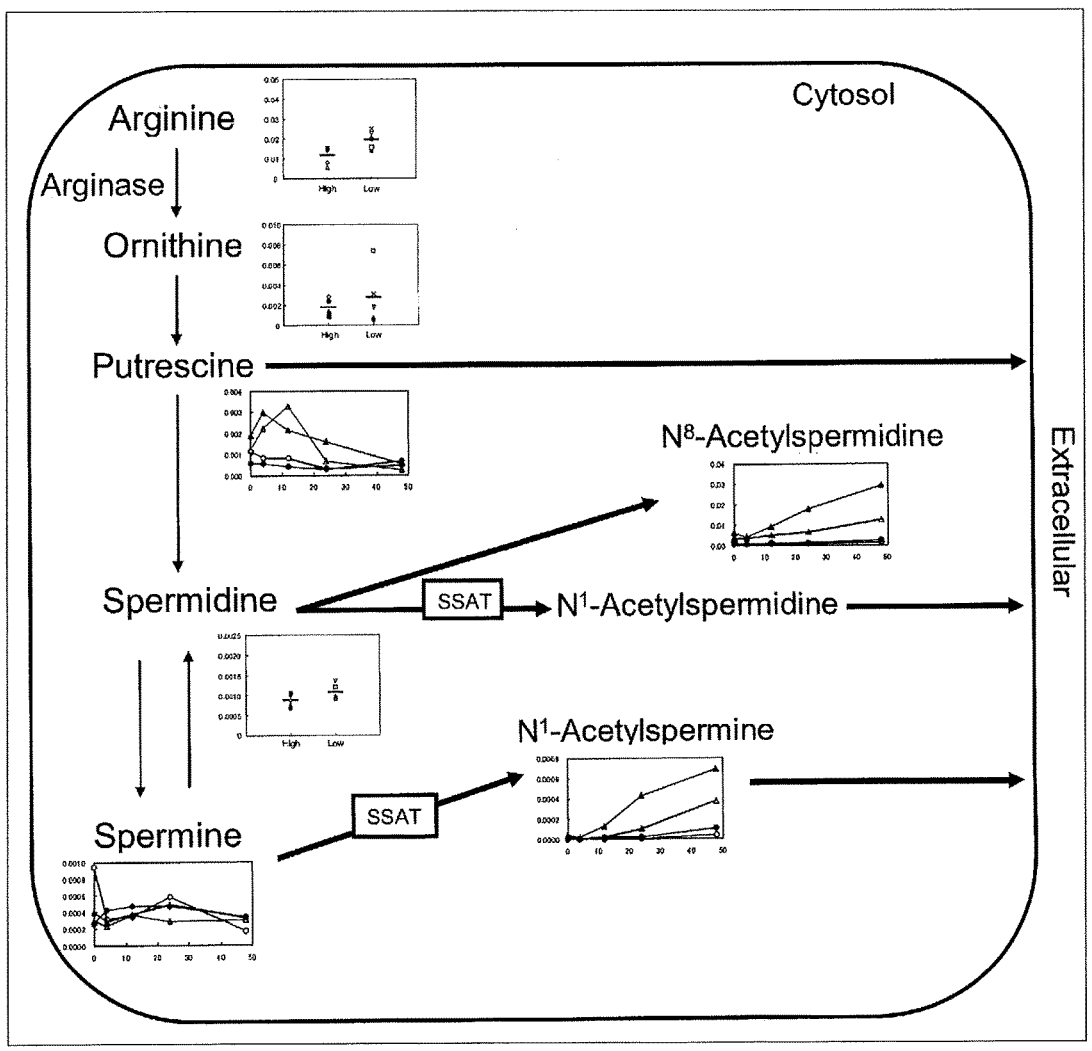
FIG. 10 A figure showing intracellular polyamine-metabolism-related substance levels in L-OHP-low-sensitivity cells and in L-OHP-high-sensitivity cells in a steady state (before drug treatment), and time-dependent profiles of intracellular polyamine-metabolism-related substance level in DLD-1 cells and that in HCT 116 cells, under exposure to L-OHP.
Figure 11:
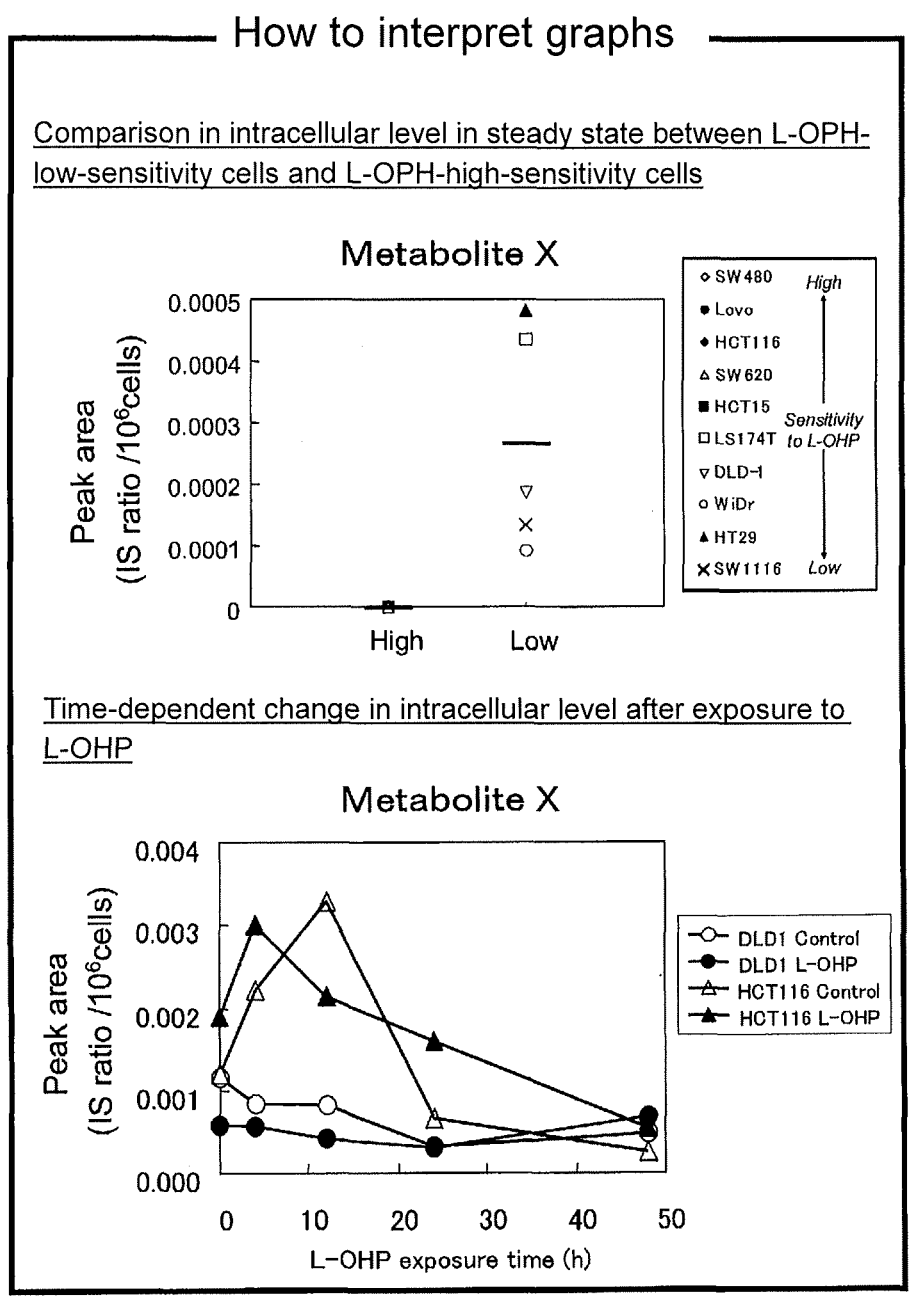
FIG. 11 Guide on how to interpret FIG. 10.

Since putrescine, $N^1$-acetylspermine, $N^8$-acetylspermidine, and spermine, which exhibited a considerable difference in time-dependent level change after exposure to L-OHP between two cell lines, and arginine found in Example 1 are compounds involved in the polyamine metabolism pathway, data of polyamine-pathway-related metabolites among the data obtained in Example 1 and 2 were further analyzed. As a result, ornithine and spermidine were found to be metabolites which exhibited a considerable difference in intracellular level between the L-OHP-high-sensitivity group and the L-OHP-low-sensitivity group (FIG. 10). FIG. 11 shows a guide on how to interpret the graphs of FIG. 10.

The variation in levels of other metabolites after 24-hour exposure to L-OHP was also investigated in L-OHP-high-sensitivity cells (HCT116) and L-OHP-low-sensitivity cells (DLD-1). As a result, some metabolites were found to exhibit a considerable rise in intracellular level in L-OHP-high-sensitivity cells after exposure to L-OHP. The metabolites were Glu, Arg, Lys, $N^6$-acetyllysine, N-acetyl-β-alanine, N-acetylornithine, γ-Glu-Cys, β-Ala-Lys, Glu-Glu, S-lactoylglutathione, cadaverine, cysteic acid, trans-cinnamic acid, S-adenosylhomocysteine, spermidine, N-acetylputrescine, guanosine, 2,3-diphosphoglyceric acid, pyruvic acid, malic acid, lauric acid, and 6-phosphogluconic acid. Also, some metabolites were found to exhibit a considerable rise in intracellular level in L-OHP-low-sensitivity cells after exposure to L-OHP. The metabolites were glutathione (GSH), butyric acid, and 4-methylpyrazole (FIG. 12).

By use of human colorectal cancer cells of two cell lines having different sensitivities to 5-FU (high-sensitivity: HCT116, low-sensitivity: DLD-1), intracellular metabolomic data after 24-hour exposure of 5-FU were analyzed, and metabolites which exhibited variation in levels after exposure to 5-FU were selected (FIG. 13). As a result, some metabolites were found to exhibit a considerable rise in intracellular level in 5-FU-high-sensitivity cells after exposure to 5-FU. The metabolites were Asp, ornithine, N-acetylornithine, β-Ala-Lys, Glu-Glu, 2-aminoadipic acid, γ-aminobutyric acid, S-adenosylhomocysteine, guanosine, CMP, UMP, 1-methyladenosine, UDP, CTP, sedoheptulose 7-phosphate, dihydroxyacetone phosphate, pyruvic acid, malic acid, $N^1$-acetylspermine, isobutylamine, and glycolic acid. Some metabolites were found to exhibit a considerable rise in intracellular level in 5-FU-low-sensitivity cells after exposure to 5-FU. The metabolites were Ser, glutathione (GSH), and adenosine. Also, some metabolites were found to exhibit a considerable drop in intracellular level in 5-FU-high-sensitivity cells after exposure to 5-FU. The metabolites were 3-methylhistidine, cadaverine, PRPP, and 4-methylpyrazole. Also, some metabolites were found to exhibit a considerable drop in intracellular level in 5-FU-low-sensitivity cells after exposure to 5-FU. The metabolites were cysteine-glutathione, 2,3-diphosphoglyceric acid, N-acetylputrescine, $N^8$-acetylspermidine, putrescine, spermidine, 6-phosphogluconic acid, NADH, and $NAD^+$.

The invention claimed is:

1. A method for determining sensitivity of a subject to fluorouracil or a salt thereof, the method comprising:
    administering fluorouracil or a salt thereof to a subject having colorectal cancer,
    measuring a level of cysteine-glutathione in a specimen derived from the subject.

2. The method of claim 1, further comprising comparing the level of cysteine-glutathione in the specimen to a standard, and administering fluorouracil or a salt thereof to the subject when the level of cysteine-glutathione in the specimen is the same or higher compared to the standard.

* * * * *